US010653709B2

(12) United States Patent
Gu et al.

(10) Patent No.: US 10,653,709 B2
(45) Date of Patent: May 19, 2020

(54) METHODS OF FOLDING A GRAFT COPOLYMER WITH DUAL ANTICANCER DRUGS AND RELATED APPLICATIONS

(71) Applicant: North Carolina State University, Raleigh, NC (US)

(72) Inventors: Zhen Gu, Apex, NC (US); Wanyi Tai, Seattle, WA (US)

(73) Assignee: North Carolina State University, Raleigh, NC (US)

(*) Notice: Subject to any disclaimer, the term of this patent is extended or adjusted under 35 U.S.C. 154(b) by 427 days.

(21) Appl. No.: 15/312,139

(22) PCT Filed: May 19, 2015

(86) PCT No.: PCT/US2015/031582
§ 371 (c)(1),
(2) Date: Nov. 17, 2016

(87) PCT Pub. No.: WO2015/179402
PCT Pub. Date: Nov. 26, 2015

(65) Prior Publication Data
US 2017/0080098 A1 Mar. 23, 2017

Related U.S. Application Data

(60) Provisional application No. 62/000,291, filed on May 19, 2014.

(51) Int. Cl.
*A61K 31/704* (2006.01)
*A61K 9/00* (2006.01)
*A61K 9/107* (2006.01)
*A61K 9/51* (2006.01)
*C08G 81/00* (2006.01)
*A61K 47/69* (2017.01)
*A61K 47/60* (2017.01)
*A61K 47/59* (2017.01)
*C08G 69/26* (2006.01)
*C08G 69/48* (2006.01)
*C08G 69/40* (2006.01)
*A61K 31/4745* (2006.01)
*A61K 47/34* (2017.01)

(52) U.S. Cl.
CPC .......... *A61K 31/704* (2013.01); *A61K 9/0019* (2013.01); *A61K 9/1075* (2013.01); *A61K 9/5146* (2013.01); *A61K 31/4745* (2013.01); *A61K 47/595* (2017.08); *A61K 47/60* (2017.08); *A61K 47/6907* (2017.08); *C08G 69/26* (2013.01); *C08G 69/40* (2013.01); *C08G 69/48* (2013.01); *C08G 81/00* (2013.01); *A61K 47/34* (2013.01)

(58) Field of Classification Search
None
See application file for complete search history.

(56) References Cited

U.S. PATENT DOCUMENTS

| 6,716,452 B1 | 4/2004 | Piccariello et al. |
| 8,426,477 B1 | 4/2013 | Breitenkamp et al. |
| 8,697,098 B2 | 4/2014 | Perumal et al. |
| 2013/0288986 A1* | 10/2013 | Davis .................. B82Y 5/00 514/20.9 |

FOREIGN PATENT DOCUMENTS

WO WO 00/64486 A2 11/2000
WO WO2004022099 * 3/2004

OTHER PUBLICATIONS

Araki et al., "A role for phosphoinositide 3-kinase in the completion of macropinocytosis and phagocytosis by macrophages," J. Cell Biol., vol. 135, No. 5, pp. 1249-1260 (Dec. 1, 1996).
Arslan, "Block and Graft Copolymerization by Controlled/Living Radical Polymerization Methods," Polymerization, Chapter 13, pp. 279, 295, and 310 (2012).
Banerjee et al., "Poly(ethylene glycol)-Prodrug Conjugates: Concept, Design, and Applications", Journal of Drug Delivery, pp. 1-17 (2012).
Berlier et al., "Quantitative Comparison of Long-wavelength Alexa Fluor Dyes to Cy Dyes: Fluorescence of the Dyes and Their Bioconjugates," J. Histochem. Cytochem., vol. 51, pp. 1699-1712 (2003).
Boon et al., "Structure/Activity Study of Tris(2-Aminoethyl)amine-Derived Translocases for Phosphatidylcholine," J. Org. Chem., vol. 67, No. 7, pp. 2168-2174 (Apr. 5, 2002).
Chen et al., "The therapeutic efficacy of camptothecin-encapsulated supramolecular nanoparticles," Biomaterials, vol. 33, No. 44, pp. 1-16 (Feb. 2012).
Duan et al., "Smart pH-Sensitive and Temporal-Controlled Polymeric Micelles for Effective Combination Therapy of Doxorubicin and Disulfiram," ACS Nano, vol. 7, No. 7, pp. 5858-5869 (2013).
Frolich, "The role of surface charge in cellular uptake and cytotoxicity of medical nanoparticle," Int.J. Nanomedicine, vol. 7, pp. 5577-5591 (2012).
Giacchetti et al., "Phase III multicenter randomized trial of oxaliplatin added to chronomodulated fluorouracil-leucovorin as first-line treatment of metastatic colorectal cancer.," J. Clin. Oncol., vol. 18, No. 1, pp. 136-147 (Jan. 2000).
Heuser et al., "Hypertonic Media Inhibit Receptor-Mediated Endocytosis by Blocking Clathrin-Coated Pit Formation," J. Cell Biol. vol. 108, No. 2, pp. 389-400 (Feb. 1989).

(Continued)

Primary Examiner — Robert A Wax
Assistant Examiner — Randeep Singh
(74) Attorney, Agent, or Firm — Jenkins, Wilson, Taylor & Hunt, P.A.

(57) ABSTRACT

A graft copolymer having drug-containing side chains is described. The graft copolymer can be prepared, for example, by directly polymerizing a drug-containing monomer on multiple sites of a linear copolymer. When exposed to water, the graft copolymer can form uniform nanocarriers, e.g., nanomicelles, optionally encapsulating additional drugs, e.g., non-covalently in the interior of the nanocarriers, for coordinated drug delivery of a plurality of drugs. Also described herein is the use of the nanocarriers for delivery of therapeutic agents, particularly the dual delivery of chemotherapeutic agents to treat tumors.

27 Claims, 7 Drawing Sheets

(56) References Cited

OTHER PUBLICATIONS

Hurwitz et al., "Bevacizumab in Combination With Fluorouracil and Leucovorin: An Active Regimen for First-Line Metastatic Colorectal Cancer." J. Clin. Oncol., vol. 23, No. 15, pp. 3502-3508 (May 20, 2005).
Notification Concerning Transmittal of International Preliminary Report on Patentability corresponding to International Application No. PCT/US2015/031582 dated Dec. 1, 2016.
Notification of Transmittal of the International Search Report and the Written Opinion of the International Searching Authority, or the Declaration corresponding to International Application No. PCT/US2015/031582 dated Sep. 3, 2015.
Kabouridis et al., "Cholesterol Depletion Disrupts Lipid Rafts and Modulates the Activity of Multiple Signaling Pathways in T Lymphocytes," Eur. J. Immunol., vol. 30, pp. 954-963 (2000).
Kaschny et al., "The components of merocyanine-540 absorption spectra in aqueous, micellar and bilayer environments," Eur.J. Biochem., vol. 207, pp. 1085-1091 (1992).
Krasnici et al., "Effect of the surface charge of liposomes on their uptake by angiogenic tumor vessels," Int. J. Cancer, vol. 105, pp. 561-567 (2003).
Lehar et al. "Synergistic drug combinations tend to improve therapeutically relevant selectivity," Nat. Biotechnol., vol. 27, No. 7, pp. 1-23 (Jul. 2009).
LoRusso et al., "Accelerating Cancer Therapy Development: The Importance of Combination Strategies and Collaboration. Summary of an Institute of Medicine Workshop," Clin. Cancer Res., vol. 18, No. 22, pp. 6101-6109 (Nov. 15, 2012).
Lu et al., "N-Trimethylsilyl Amines for Controlled Ring-Opening Polymerization of Amino Acid N-Carboxyanhydrides and Facile End Group Functionalization of Polypeptides," J. Am. Chem. Soc., vol. 130, pp. 12562-12563 (2008).
Maughan et al., "Addition of cetuximab to oxaliplatin-based firstline combination chemotherapy for treatment of advanced colorectal cancer: results of the randomised phase 3 MRC COIN trial.," Lancet, vol. 377, pp. 2103-2114 (Jun. 18, 2011).
Moretton et al., "Cryoprotection-lyophilization and physical stabilization of rifampicin-loaded flower-like polymeric micelles," J. R. Soc. Interface, 9, 487-502 (2012).
nanoComposix, "nanoComposix's Guide to Dynamic Light Scattering Measurement and Analysis," Guidelines for Dynamic Light Scattering Measurement and Analysis, v 1.3, pp. 1-7 (Sep. 2012).
Nishimura et al., "Combinatorial Targeting of the Macropinocytotic Pathway in Leukemia and Lymphoma Cells," J. Biol. Chem., vol. 283, No. 17, pp. 11752-11762 (Apr. 25, 2008).
Orth et al., "Genetic instability in human ovarian cancer cell lines," Proc. Natl. Acad. Sci. USA, vol. 91, pp. 9495-9499 (Sep. 1994).
Patist et al., "On the Measurement of Critical Micelle Concentrations of Pure and Technical-Grade Nonionic Surfactants," J. Surfact Deterg., vol. 3, No. 1, pp. 53-58 (Jan. 2000).
Plumb et al., "Effects of the pH Dependence of 3-(4,5-Dimethylthiazol-2-Yl)-2,5-Diphenyl-Tetrazolium Bromide-Formazan Absorption on Chemosensitivity Determined by a Novel Tetrazolium-Based Assay," Cancer Res., vol. 49, No. 16, pp. 4435-4440 (Aug. 1989).
Saltz et al., "Bevacizumab in Combination With Oxaliplatin-Based Chemotherapy As First-Line Therapy in Metastatic Colorectal Cancer: A Randomized Phase III Study," J. Clin. Oncol., vol. 26, No. 12, pp. 2013-2019 (2008).
Singh et al., "Selective Caveolin-1-dependent Endocytosis of Glycosphingolipids," Mol. Biol. Cell., vol. 14, pp. 3254-3265 (Aug. 2003).
Sung et al., "Effects of static quenching and light pulse intensity on the time-dependent fluorescence quenching kinetics, " Chem Phys., vol. 179, pp. 23-37 (1994).
Tai et al., "Development of a peptide-drug conjugate for prostate cancer therapy," Mol. Pharm., vol. 8, No. 3, pp. 1-25 (Jun. 6, 2011).

Tai et al., "Expression profile and functional activity of peptide transporters in prostate cancer cells," Mol. Pharm., vol. 10, No. 2, pp. 1-26 (Feb. 4, 2013).
Tsai et al., "Graft and diblock copolymer multifunctional micelles for cancer chemotherapy and imaging," Biomaterlals, vol. 31, pp. 2293-2301 (2010).
Veronese et al., "PEGylation,successful approach to drug delivery," Drug Discovery Today (DDT), vol. 10, No. 21, pp. 1451-1458 (Nov. 2005).
Wall et al., "Camptothecin and Taxol: Discovery to Clinic-Thirteenth Bruce F. Cain Memorial Award Lecture," Cancer Research, vol. 55, pp. 753-760 (Feb. 15, 1995).
Wang et al., "Mis-assembly of clathrin lattices on endosomes reveals a regulatory switch for coated pit formation," J. Cell Biol., vol. 123, No. 5, pp. 1107-1117 (Dec. 1993).
Basu et al., "Photophysical studies of Merocyanine 540 dye in aqueous micellar dispersions of different surfactants and in different solvents," Spectrochim Acta Part A, vol. 66, pp. 1255-1260 (2007).
Benito et al., "Optimizing saccharide-directed molecular delivery to biological receptors: design, synthesis, and biological evaluation of glycodendrimer-cyclodextrin conjugates," J. Am. Chem. Soc., vol. 126, No. 33, pp. 10355-10363 (2004).
Beretta et al., "Mechanisms of Cellular Resistance to Camptothecins," Curr. Med. Chem., vol. 13, pp. 3291-3305 (2006).
Berge et al., "Pharmaceutical Salts," J. Pharm. Sci., vol. 66, No. 1, pp. 1-19 (Jan. 1977).
Binaschi et al., "Mechanism of Action of DNA Topoisomerase Inhibitors," Stem Cells, vol. 13, pp. 369-379 (1995).
Chen et al., "The accumulation of dual pH and temperature responsive micelles in tumors," Biomaterials, vol. 33, pp. 4576-4588 (2012).
Deming et al., "Chain initiation efficiency in cobalt-and nickelmediated polypeptide synthesis," J. Am. Chem. Soc., 122, 5710-5717 (2000).
Ding et al., "Toward the next-generation nanomedicines: Design of multifunctional multiblock polyurethanes for effective cancer treatment," ACS Nano, vol. 7, No. 3, pp. 1918-1928 (2013).
He et al., "Effects of particle size and surface charge on cellular uptake and biodistribution of polymeric nanoparticles," Biomaterials, vol. 31, pp. 3657-3666 (2010).
Kataoka et al., "Doxorubicin-loaded poly(ethylene glycol)-poly(beta-benzyl-L-aspartate) copolymer micelles: their pharmaceutical characteristics and biological significance," J. Control Release, vol. 64, pp. 143-153 (2000).
Kedar, et al., "Advances in polymeric micelles for drug delivery and tumor targeting," Nanomedicine: Nanotechnology, Biology, and Medicine, vol. 6, No. 6, pp. 714-729 (Dec. 2010).
Lengauer et al., "Genetic instabilities in human cancers," Nature, vol. 396, pp. 643-649 (Dec. 17, 1998).
Saleem et al., "Mechanisms of Resistance to Camptothecins," Ann. N.Y. Acad. Sci., vol. 922, pp. 46-55 (2000).
Schluep et al., "Preclinical Efficacy of the Camptothecin-Polymer Conjugate IT 101inMultiple Cancer Models," Clin. Cancer Res., Voo. 12, No. 5, pp. 1606-1614 (Mar. 1, 2006).
Shuai et al., "Micellar carriers based on block copolymers of poly(ε-caprolactone) and poly(ethylene glycol) for doxorubicin delivery," J. Control Release, vol. 98, pp. 415-426 (2004).
Singer et al., "Water-soluble poly-(I-glutamic acid)-gly-camptothecin conjugates enhance camptothecin stability and efficacy," J. Control Release, vol. 74, pp. 243-247 (2001).
Tai et al., "A Novel Rapamycin-Polymer Conjugate Based on a New Poly(Ethylene Glycol) Multiblock Copolymer," Pharmaceutical Research, vol. 31, pp. 706-719 (2014).
Tai et al., "Inhibition of breast cancer cell growth and invasiveness by dual silencing of HER-2 and VEGF," Molecular pharmaceutics, vol. 7, No. 2, pp. 543-556 (2010).
Wall et al., "Camptothecin: Discovery to Clinic," Ann. N.Y. Acad. Sci., 803, 1-12 (1996).
Xiao et al., "Role of cellular uptake in the reversal of multidrug resistance by PEG-b-PLA polymeric micelles," Biomaterials, vol. 32, pp. 5148-5157 (2011).

* cited by examiner

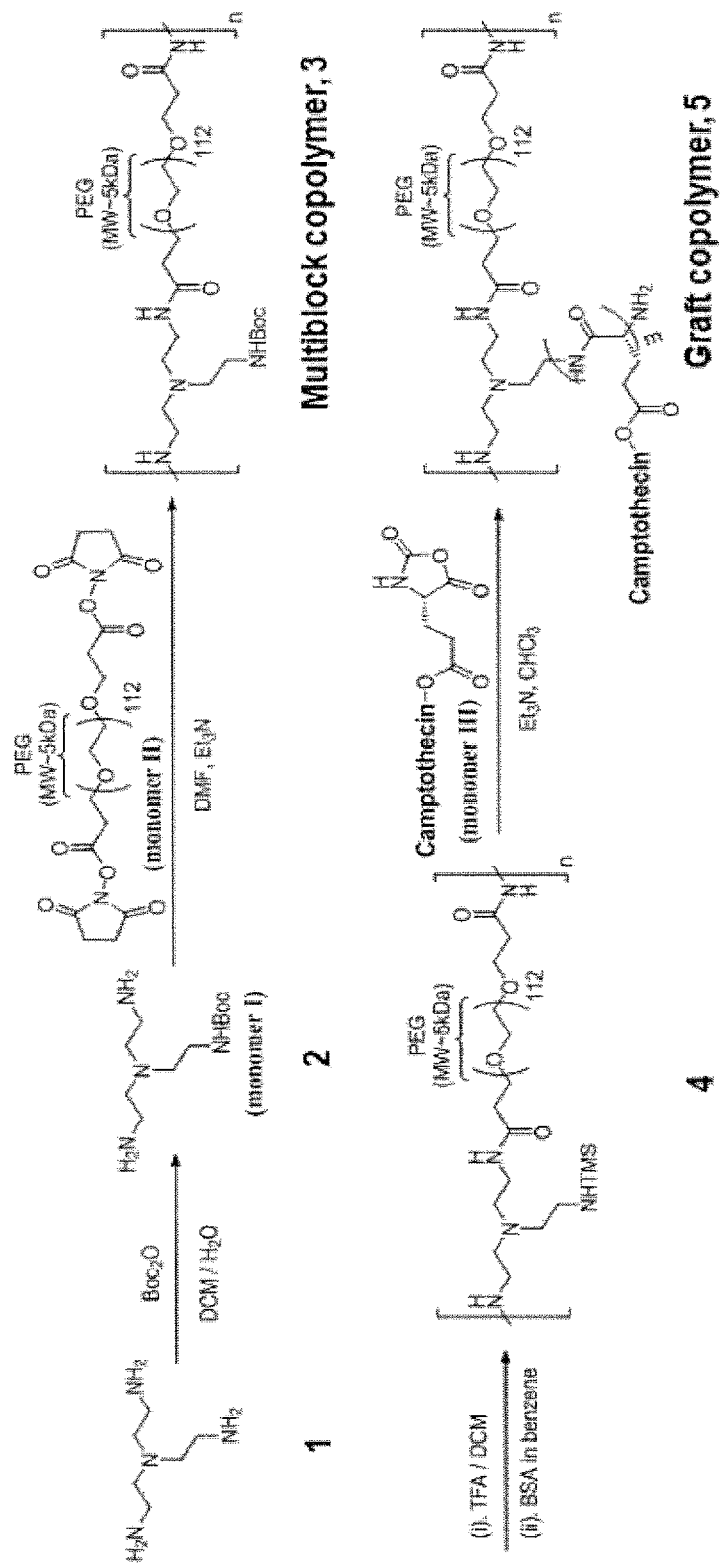
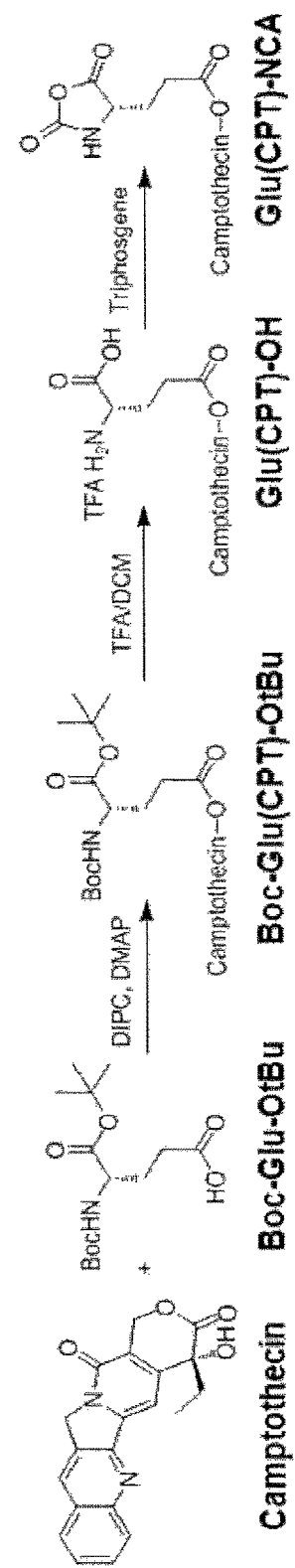
FIG. 2A
FIG. 2B

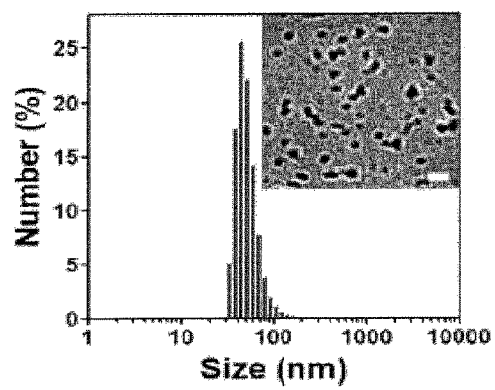
FIG. 3A
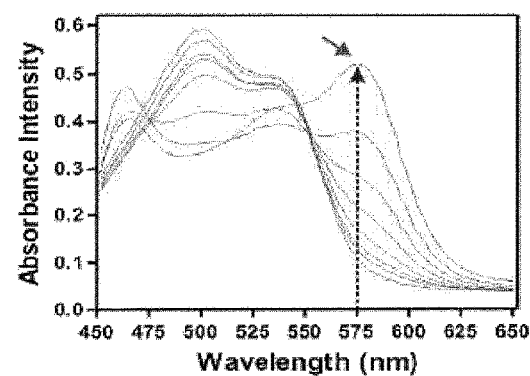
FIG. 3B
FIG. 3C
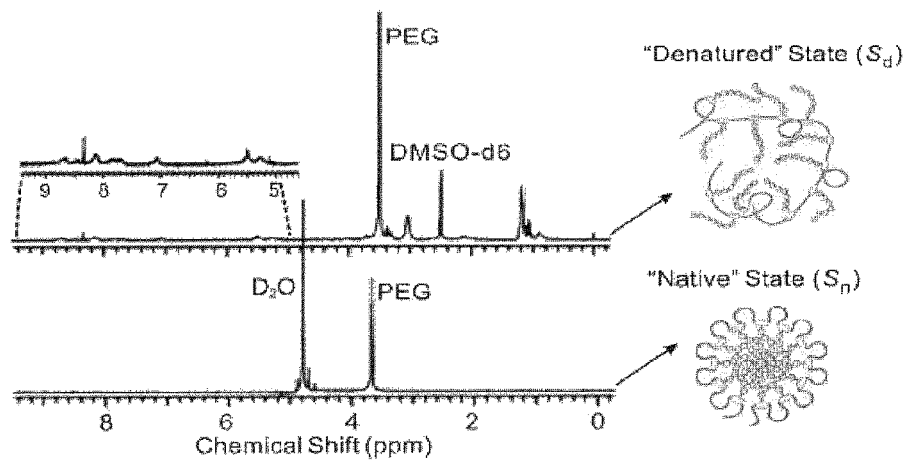

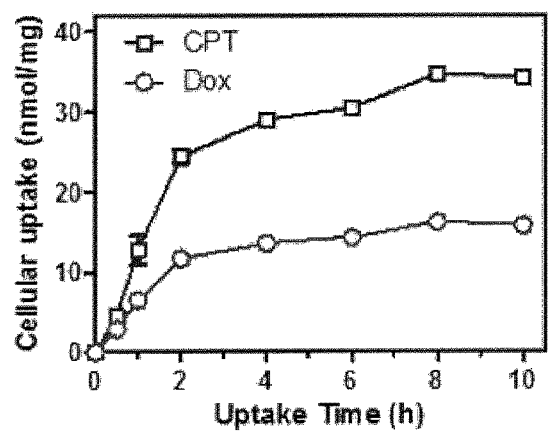 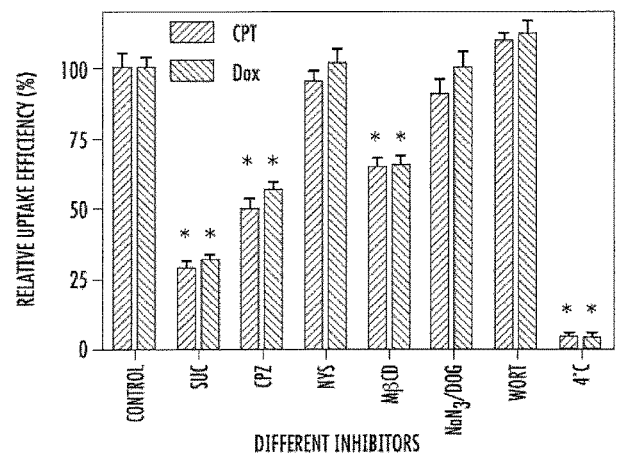
FIG. 6A                               FIG. 6B

METHODS OF FOLDING A GRAFT COPOLYMER WITH DUAL ANTICANCER DRUGS AND RELATED APPLICATIONS

RELATED APPLICATIONS

The presently disclosed subject matter claims the benefit of U.S. Provisional Patent Application No. 62/000,291, filed May 19, 2014, the disclosure of which is incorporated herein by reference in its entirety.

TECHNICAL FIELD

The presently disclosed subject matter relates to a graft copolymer for the delivery of therapeutic agents, such as chemotherapeutic agents, and/or the co-delivery of a plurality such therapeutic agents. The presently disclosed subject matter further relates to the preparation of the graft copolymer and to the use of the graft copolymer in treating diseases, such as cancer.

ABBREVIATIONS

° C.=degrees Celsius
%=percentage
µL=microliter
µmol=micromole
BOC=t-butoxycarbonyl
CMC=critical micelle concentration
CPT=camptothecin
DLS=dynamic light scattering
DMF=dimethylformamide
Dox=doxorubicin
g=gram
h=hour
kD=kiloDalton
kg=kilogram
mg=milligram
min=minute
mL=milliliter
mm=millimeter
mM=millimolar
mmol=millimole
$M_n$=number average molecular mass
$M_w$=mass average molecular mass
MW=molecular weight
nm=nanometer
NMP=N-methylpyrrolidone
NMR=nuclear magnetic resonance
PBS=phosphate buffered saline
PDI=particle size polydispersity or particle size polydispersity index
PEG=poly(ethylene glycol)
ppm=parts-per-million
ROP=ring opening polymerization
$S_d$=denatured state
$S_n$=native state
tBu=tert-butyl
TEM=transmission electron microscopy
TFA=trifluoroacetic acid
TLC=thin layer chromatography
TMS=trimethylsilyl
Top=topoisomerase
wt=weight

BACKGROUND

Cancer cells contain a genetically unstable chromosome and hold a tendency to evolve in response to drug challenges. See Lengauer et al., Nature, 396, 643-649 (1998); and Orth et al., Proc. Natl. Acad. Sci. U.S.A., 91, 9495-9499 (1994). Patients treated with a single agent often develop resistance even if showing an initial response. The use of a combination of multiple drugs (i.e., "combinational chemotherapy") can offer the potential benefit of simultaneously inhibiting several anti-cancer targets and therefore preventing or delaying the emergence of drug resistance. See LoRusso et al., Clin. Cancer Res., 18, 6101-6109 (2012). Combinational chemotherapy has been adopted as the first-line treatment of many advanced cancers. See Saltz et al., J. Clin. Oncol., 26, 2013-2019 (2008); Maughan et al., Lancet, 377, 2103-2114 (2011); Giacchetti et al., J. Clin. Oncol., 18, 136 (2000); Hurwitz et al., J. Clin. Oncol., 23, 3502-3508 (2005). However, the difference in solubility, potency, pharmacokinetics and bioavailability among drugs can make the dose schedule for combinatorial chemotherapy challenging. See Duan et al., ACS Nano, 7, 5858-5869 (2013); Lehar et al., Nat. Biotechnol., 27, 659-666 (2009); and Tai et al., Mol. Pharm., 7, 543-556 (2010). Moreover, simple noncovalent encapsulation of multiple agents into a single particle can lead to untunable drug composition and uncontrollable and/or premature release of drug.

Accordingly, there is still an ongoing need in the art for additional drug delivery agents, such as agents to deliver multiple drugs for combinational chemotherapy. More particularly, there is an ongoing need for multi-drug delivery agents that are easy to prepare in large scale manufacturing, that can provide a tunable drug loading ratio to provide a precise dose schedule, that can have stealth properties to decrease macrophage clearance and avoid immune system attack, and/or that have high drug loading capacity.

SUMMARY

In some embodiments, the presently disclosed subject matter provides a graft copolymer drug conjugate, wherein said graft copolymer drug conjugate comprises a linear copolymeric main chain and a plurality of polymeric side chains, wherein each polymeric side chain comprises a plurality of at least a first therapeutic agent covalently attached thereto.

In some embodiments, each polymeric side chain comprises a plurality of first therapeutic agent-containing monomeric units, wherein each of said first therapeutic agent-containing monomeric units comprises a divalent chemical moiety further comprising a covalently attached first therapeutic agent. In some embodiments, the first therapeutic agent is covalently attached to the polymeric side chain via a linkage that can be enzymatically cleaved and/or that can be cleaved under physiological conditions at a desired location in viva In some embodiments, the first therapeutic agent is covalently attached via a linkage that can be cleaved via an intracellular esterase.

In some embodiments, the first therapeutic agent is selected from the group comprising a chemotherapeutic agent, an anti-viral agent, an anti-inflammatory agent, an analgesic agent, an anesthetic, an antifungal agent, an antibiotic, an antihypertensive, an antimicrobial, an antipyretic, a cardioactive agent, a vasoconstrictor, a vasodilator, a nutritional supplement, a antiarthritic, a diuretic, a hormone, a radiation sensitizer, a sedative and a therapeutic biological agent, such as a peptide or small interfering RNA (siRNA). In some embodiments, the first therapeutic agent is a small molecule chemotherapeutic agent, optionally wherein the chemotherapeutic agent is a topoisomerase (Top) inhibitor. In some embodiments, the first therapeutic agent is camptothecin.

In some embodiments, the graft copolymer drug conjugate has the formula:

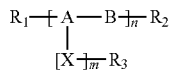

wherein: A is a trivalent moiety; B comprises a hydrophilic polymeric moiety; X is a divalent moiety comprising a covalently attached first therapeutic agent; n is an integer between 4 and 25; m is an integer between 5 and 30; and each of $R_1$, $R_2$, and $R_3$ is a monovalent moiety.

In some embodiments, A is derived from a trifunctional monomer comprising three chemically reactive functional groups wherein each of the three functional groups is independently selected from the group comprising hydroxyl, amino, thiol, alkyl or aryl disulfide, isothiocyanate, thiocarbonylimidazole, thiocarbonylchloride, aldehyde, ketone, carboxylic acid, carboxylic acid ester, sulfonic acid, sulfonic acid ester, sulfonyl chloride, phosphoric acid, alkyl or aryl succinimidyl carbonate, alkyl or aryl chlorocarbonate, alkyl or aryl succinimidylthiocarbonate, alkyl or aryl chlorothiocarbonate, halide, and thioester. In some embodiments, A is derived from a natural or non-natural amino acid or from a tris(aminoalkyl)amine, optionally tris(aminoethyl)amine.

In some embodiments, the hydrophilic polymeric moiety is selected from the group comprising poly(alkylene glycol), poly(vinyl alcohol), poly(2-hydroxyethyl methacrylate), poly[N-(2-hydroxypropyl)methacrylamide] (PHPMA), poly(acrylic acid), poly(methacrylic acid), poly(maleic acid), polylysine, dextran, chitosan, alginate, hyaluronic acid, and combinations thereof. In some embodiments, B comprises a poly(ethylene glycol) (PEG), such as $PEG_{500}$.

In some embodiments, X is derived from a monomer that comprises a moiety that can undergo ring opening polymerization, optionally wherein the moiety that can undergo ring opening polymerization is a cyclic moiety that comprises one or more heteroatoms, such as an epoxide, an aziridine, an episulfide, a lactone, a lactam, or a cyclic anhydride. In some embodiments, X is derived from a monomer comprising the N-carboxyanhydride derived from an amino acid-first therapeutic agent conjugate, wherein said amino acid-first therapeutic agent conjugate comprises an amino acid covalently attached to the first therapeutic agent via a functional group on the amino acid side chain, optionally wherein the amino acid is glutamic acid and the amino acid-first therapeutic agent conjugate is glutamic acid covalently attached to the first therapeutic agent via the carboxylic acid side chain.

In some embodiments, each of $R_1$, $R_2$, and $R_3$ is independently selected from the group comprising H, OH, $NH_2$, alkyl, aralkyl, aryl, acyl, a hydroxy protecting group, an amino protecting group and a fluorescent label or other detectable group. In some embodiments, the graft copolymer drug conjugate has the formula:

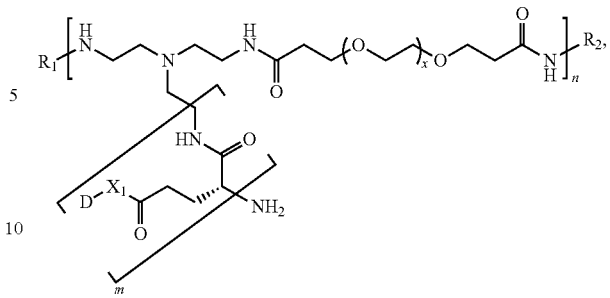

wherein: n is an integer between 4 and 25; m is an integer between 5 and 30; x is an integer between 10 and 200, optionally wherein x is 112; $X_1$ is O, S, or NH; D is a monovalent moiety derived from the first therapeutic agent; and $R_1$ and $R_2$ are each monovalent moieties.

In some embodiments, the graft copolymer drug conjugate comprises between about 10 and about 30 weight percentage (%) of the first therapeutic agent, optionally between about 15 and about 25 weight % of the first therapeutic agent. In some embodiments, the graft copolymer drug conjugate has a mass average molecular mass ($M_w$) between about 30,000 g/mol and about 40,000 g/mol. In some embodiments, the graft copolymer drug conjugate has a critical micelle concentration (CMC) of between about 0.002 mg/mL and about 0.003 mg/mL, optionally between about 0.0023 mg/mL and about 0.0025 mg/mL.

In some embodiments, the presently disclosed subject matter provides a polymeric micelle comprising the graft copolymer drug conjugate. In some embodiments, the polymeric micelle has a particle size polydispersity index (PDI) of between about 0.1 and about 0.2, optionally between about 0.13 and about 0.17.

In some embodiments, the polymeric micelle further comprises at least a second therapeutic agent encapsulated non-covalently within the micelle. In some embodiments, the first and second therapeutic agents are both chemotherapeutic agents. In some embodiments, the first and second therapeutic agents are both topoisomerase (Top) inhibitors, optionally wherein the first therapeutic agent is a Top I inhibitor and the second therapeutic agent is a Top II inhibitor. In some embodiments, the first therapeutic agent is camptothecin and the second therapeutic agent is doxorubicin. In some embodiments, the polymeric micelle comprises up to about 30 weight percentage (%) of the second therapeutic agent (compared to the weight of graft copolymer drug conjugate), optionally comprising about 10 weight % of the second therapeutic agent.

In some embodiments, the polymeric micelle has an average diameter of between about 10 nm and about 100 nm, optionally between about 25 nm and about 75 nm, or optionally between about 50 nm and about 70 nm.

In some embodiments, the presently disclosed subject matter provides a pharmaceutical composition comprising a pharmaceutically acceptable carrier and a graft copolymer drug conjugate, wherein the graft copolymer drug conjugate comprises a linear copolymeric main chain and a plurality of polymeric side chains, wherein each polymeric side chain comprises a plurality of at least a first therapeutic agent covalently attached thereto. In some embodiments, the presently disclosed subject matter provides a pharmaceutical composition comprising a polymeric micelle comprising said graft copolymer drug conjugate, and further comprising a pharmaceutically acceptable carrier. In some embodiments, the polymeric micelle comprises a covalently attached first therapeutic agent and an encapsulated second therapeutic agent, and the first and second therapeutic agents have different release profiles, optionally wherein the second therapeutic agent has a rapid release profile and the first therapeutic agent has a sustained release profile.

In some embodiments, the presently disclosed subject matter provides a method of treating a disease in a subject in need thereof, the method comprising administering to the subject a pharmaceutical composition comprising a graft copolymer drug conjugate or a polymeric micelle as described herein, optionally wherein the subject is a mammal, such as a human, further optionally wherein the composition is administered intravenously. In some embodiments, the disease is cancer, optionally breast cancer, lung cancer, liver cancer, prostate cancer, cervical cancer, or leukemia.

In some embodiments, the presently disclosed subject matter provides a method of treating cancer in a subject in need thereof, the method comprising administering to the subject a polymeric micelle comprising a graft copolymer drug conjugate as described herein. In some embodiments, the polymeric micelle comprises a second therapeutic agent encapsulated within the micelle and wherein the first and second therapeutic agents are both chemotherapeutic agents.

In some embodiments, the first and second therapeutic agents are both topoisomerase (Top) inhibitors, optionally wherein the first therapeutic agent is a Top I inhibitor and the second therapeutic agent is a Top II inhibitor. In some embodiments, the first therapeutic agent is camptothecin and the second therapeutic agent is doxorubicin.

In some embodiments, the first and second therapeutic agents have synergistic effects and/or the micelle preferentially accumulates in cancer cells when administered to the subject as compared to non-cancerous heart, spleen and/or kidney cells.

In some embodiments, the presently disclosed subject matter provides a method of preparing a graft copolymer drug conjugate, wherein the method comprises: (a) contacting a first monomer and a second monomer in a first solvent to provide a linear copolymer, wherein the first monomer comprises a partially protected trifunctional compound, wherein the partially protected trifunctional compound comprises three chemically reactive groups, wherein each of said chemically reactive groups can be the same or different and wherein one of said three chemically reactive groups is protected with a protecting group, and wherein the second monomer is a bifunctional derivative of a hydrophilic polymer, optionally wherein the bifunctional derivative is a hydrophilic polymer comprising two activated esters; (b) contacting the linear copolymer with a deprotecting reagent to remove the protecting group, thereby providing a deprotected linear copolymer; and (c) contacting the deprotected linear copolymer with a third monomer in a second solvent, wherein the third monomer comprises a polymerizable group and a covalently attached first therapeutic agent, thereby providing a graft copolymer comprising a plurality of first therapeutic agents.

In some embodiments, the polymerizable group of the third monomer can undergo ring opening polymerization, optionally wherein the polymerizable group is a cyclic moiety comprising a heteroatom. In some embodiments, the third monomer is a N-carboxyanhydride derived from an amino acid-first therapeutic agent conjugate, wherein said amino acid-first therapeutic agent conjugate comprises an amino acid covalently attached to the first therapeutic agent via a functional group on the amino acid side chain, optionally wherein the amino acid is glutamic acid and the amino acid-first therapeutic agent conjugate is glutamic acid covalently attached to the first therapeutic agent via the glutamic acid carboxylic acid side chain.

In some embodiments, the second monomer is a bis-N-hydroxysuccinimide ester of a poly(ethylene glycol) (PEG), optionally wherein the PEG is $PEG_{500}$. In some embodiments, the first monomer is a mono-protected tris(aminoalkyl)amine, optionally wherein the first monomer is N,N-bis(2-aminoethyl)-N-[2-(tert-butylcarbamoyl)ethyl]amine.

In some embodiments, the first solvent is a polar, aprotic solvent, optionally dimethylformamide (DMF). In some embodiments, the second solvent is a non-polar solvent, optionally chloroform.

In some embodiments, the first monomer and the second monomer are contacted in a 1/1 molar ratio in step (a). In some embodiments, the protecting group comprises a tert-butoxycarbonyl group and the deprotecting reagent is trifluoracetic acid (TFA).

In some embodiments, the method further comprises activating the deprotected linear copolymer, optionally wherein the activating comprises preparing a trimethylsilyl (TMS) derivative. In some embodiments, between about 5 and about 35 molar equivalents of the third monomer are contacted with one molar equivalent of the linear copolymer, optionally wherein about 20 equivalents of the third monomer are contacted with the linear copolymer.

In some embodiments, the method further comprises preparing a solution of the graft copolymer in an organic solvent and mixing the solution with water, thereby providing micelles of the graft copolymer. In some embodiments, preparing the solution of the graft copolymer in the organic solvent further comprises dissolving a second therapeutic agent in the solution, wherein when the solution is mixed with water, micelles are formed with the second therapeutic agent encapsulated therein. In some embodiments, the organic solvent is N-methylpyrrolidone (NMP).

It is an object of the presently disclosed subject matter to provide graft copolymers drug conjugates, micelles and/or pharmaceutical compositions thereof, as well as to provide methods of preparing the conjugates and methods of using the conjugates to treat disease. An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 2A is a schematic drawing showing the synthesis of the graft co-polymer described for FIG. 1B, including chemical structures of exemplary monomers and reagents.

FIG. 2B is a schematic scheme showing the synthesis of a camptothecin (CPT)-containing monomer, i.e., Glu(CPT)-NCA), for use in ring-opening polymerization reactions. The monomer is based on the N-carboxyanhydride (NCA) of glutamic acid (Glu). The CPT is covalently attached to the carboxylic acid side chain of the Glu-NCA via an ester linkage.

FIG. 3A is a graph of the hydrodynamic size (in nanometers, nm) of folded nanocarrier formed from a presently disclosed graft copolymer prepared using a feed ratio of drug-containing monomer to linear copolymer of 20/1 (i.e., MB-20), folded in the presence of doxorubicin (Dox). The hydrodynamic size of the nanocarrier, also referred to as MB-20/Dox, was measured by dynamic light scattering (DLS). Inset is a transmission electron micrograph of the nanocarrier. The white scale bar in the lower right-hand corner of the inset corresponds to 100 nm.

FIG. 3B is a graph showing the absorbance spectra of merocyanine540 in an aqueous solution of the graft copolymer nanocarrier described for FIG. 3A. The maximum wavelength ($\lambda_{max}$) shifted toward 575 nanometers (nm) (see grey arrow) as the polymer concentration increased (from bottom to top: 0 to 1 milligrams per milliliter, see black dotted line arrow).

FIG. 3C is a pair of hydrogen nuclear magnetic resonance (NMR) spectra of the graft copolymer nanocarrier described for FIG. 3A. The upper spectra is for the graft copolymer in deuterated dimethylsulfoxide (DMSO-$d_6$), thus showing the spectra of the nanocarrier in a "denatured" state ($S_d$). The lower spectra is in deuterated water ($D_2O$), thus showing the spectra of the folded nanocarrier, also referred to herein as the "native" state ($S_n$). The inset shows the NMR signals of camptothecin in the copolymer side chains of the nanocarrier.

FIG. 6A is a graph showing the cellular uptake (nanomoles(nmol)/milligram(mg)) of therapeutic agents from a presently disclosed dual-delivery nanocarrier (formed from a graft copolymer prepared using a feed ratio of camptothecin (CPT)-containing monomer to linear copolymer of 20/1; MB-20) in cancer cells (A549 cells) over time (0 to 10 hours). Uptake of doxorubicin (Dox) is shown in circles, while uptake of camptothecin (CPT) is shown in squares.

FIG. 6B is a bar graph showing the relative uptake efficiency of chemotherapeutic agents from a presently disclosed dual-delivery nanocarrier (formed from a graft copolymer prepared using a feed ratio of camptothecin (CPT)-containing monomer to linear copolymer of 20/1; MB-20) in cancer cells (A549 cells) in the presence of various endocytosis inhibitors: sucrose (SUC), chlopromazine (CPZ), nystatin (NYS), methyl-β-cyclodextrin (MβCD), sodium azide/2-deoxyglucose ($NaN_3$/DOG), wortmannin (WORT). Uptake of CPT is shown in the bars with lines going from the bottom left to the top right, while that of doxorubicin (Dox) by the bars with lines going from the top left to the bottom right. *P<0.01 with respect to control groups.

DETAILED DESCRIPTION

Figure 1A:
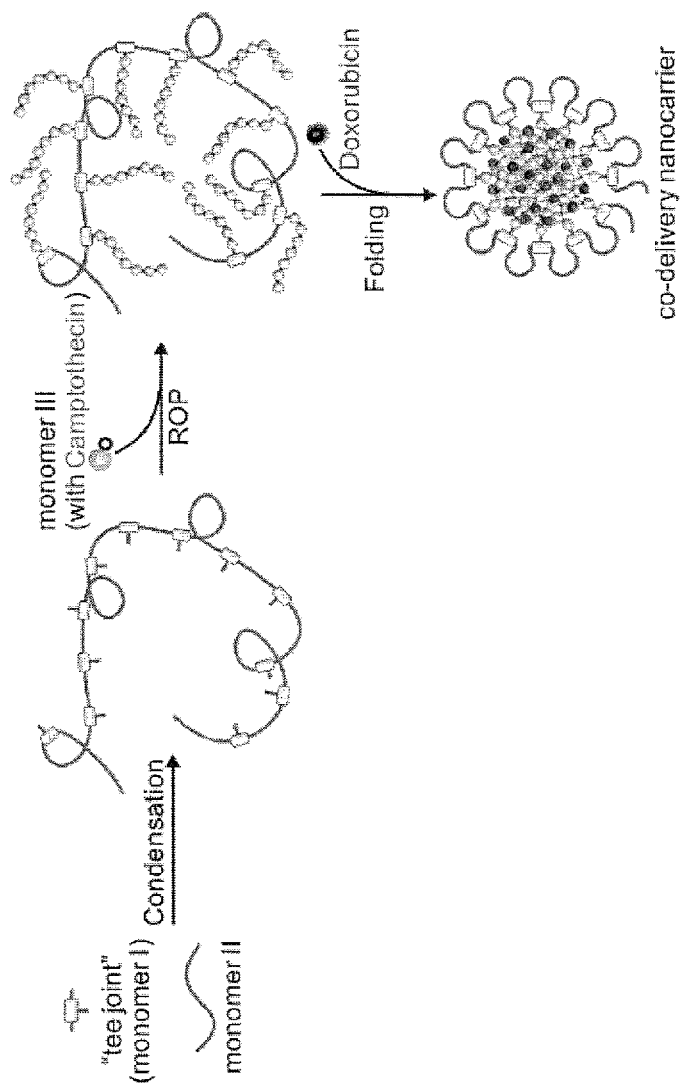
FIG. 1A is a schematic drawing showing the preparation of a nanocarrier for the co-delivery of two chemotherapeutic agents, i.e., camptothecin and doxorubicin, according to an embodiment of the presently disclosed subject matter. The preparation of the nanocarrier comprises the condensation of monomers I and II to form a linear block copolymer. Monomer I can act as a "tee-joint" and has a site that can be the initiation site for ring-opening polymerization (ROP) of monomer III to form polymeric side chains grafted off of the linear block copolymer. Monomer III also includes one of the two chemotherapeutic agents, i.e., camptothecin, e.g, covalently attached. Following the addition of the side chains via ROP, the resulting graft copolymer is folded to form a nanocarrier. During folding, the second chemotherapeutic agent, i.e., doxorubicin, is incorporated, e.g., non-covalently, in the interior space of the nanocarrier.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All publications, patent applications, patents, and other references mentioned herein are incorporated by reference in their entirety.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims.

Unless otherwise indicated, all numbers expressing quantities of reagents, reaction conditions, weight %, diameter, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of mass, weight, concentration or percentage is meant to encompass variations of in one example ±20% or ±10%, in another example ±5%, in another example ±1%, and in still another example ±0.1% from the specified amount, as such variations are appropriate to perform the disclosed methods.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, Pert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted (e.g., with an alkyl or aryl group substituent).

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "acyl" refers to the —C(=O)R group, wherein R is H, alkyl, aralkyl or aryl, wherein the alkyl, aralkyl, or aryl group is optionally substituted with an alkyl and/or aryl group substituent.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl. "Arylamine" and "aminoaryl" refer to the group —N(R)$_2$ wherein each R is H, aryl, or substituted aryl, and wherein at least one R is aryl or substituted aryl, e.g., aniline (i.e., —NHC$_6$H$_5$). The term "primary amine" refers to —NH$_2$ group.

The terms "halo", "halide", or "halogen" as used herein refer to fluoro, chloro, bromo, and iodo groups.

The term "hydroxyl" refers to the —OH group.

The terms "mercapto" or "thiol" refer to the —SH group.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane (DCM), diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and halogenated hydrocarbons, such as carbon tetrachloride, DCM, and chloroform.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "nanocarrier" as used herein refer to a structure (e.g., a nanoparticle and/or micelle) having at least one region with a dimension (e.g., length, width, diameter, etc.) of less than about 1,000 nm and that comprises one or more therapeutic agents (e.g. covalently or non-covalently associated with the nanocarrier). In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

In some embodiments, the nanocarrier is approximately spherical. When the nanocarrier is approximately spherical, the characteristic dimension can correspond to the diameter of the sphere. In addition to spherical shapes, the nanocarrier can be disc-shaped, oblong, cylindrical, elliptical, polyhedral, rod-shaped, cubic, or irregularly-shaped. A nanocarrier can also comprise clusters of spheres, rods, discs, or cubes.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering (DLS).

"Monodisperse" is used herein to describe a population of polymers or particles where all of the polymers or particles are the same or nearly the same molecular weight or size. For example, "monodisperse" can refer to molecular weight or particle size distributions in which 90% of the distribution lies within 15%, 10% or 5% of the median molecular weight or particle size. In some embodiments, "monodisperse" can refer to a population with a particle size polydispersity index (PDI) that is about 0.1 or less. In some embodiments, "near monodisperse" or "substantially monodisperse" can refer to a population with a PDI of between about 0.2 and about 0.1, wherein PDI is the square of the standard deviation/mean hydrodynamic diameter of the particles.

As used herein, a "monomer" or "polymerizable monomer" can refer to a molecule that can undergo polymerization, thereby contributing constitutional units, i.e., an atom or group of atoms, to the essential structure of a macromolecule. A polymerizable monomer is a molecule that comprises one or more reactive moieties {e.g., siloxy ethers, hydroxyls, amines, vinylic groups (i.e., carbon-carbon double bonds), halides (i.e., CI, Br, F, and I), esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material.

An "oligomer" refers to a molecule of intermediate relative molecular mass, the structure of which comprises a small plurality of units (e.g., 2-5 or 2-9) derived from molecules of lower relative molecular mass.

The terms "polymer" and "polymeric" refer to chemical structures that have repeating units (i.e., multiple copies of a given chemical substructure). As used herein, in some embodiments, polymers can refer to compounds having more than 10 repeating units and/or to compounds wherein the repeating unit is other than methylene. However, in some embodiments, polymer can also refer to oligomers, as well as to compounds with larger numbers of repeating units. Polymers can be formed from polymerizable monomers. Some polymers contain biodegradable linkages, such as esters or amides, such that they can degrade overtime under biological conditions.

A "copolymer" refers to a polymer derived from more than one species of monomer.

As used herein, a "block copolymer" refers to a copolymer that comprises blocks (i.e., polymeric sub-sections of the whole copolymer), e.g., in a linear sequence. A "block" refers to a portion of a copolymer that has at least one feature that is not present in the adjacent portions of the macromolecule. Thus, a "block copolymer" can refer to a copolymer in which adjacent blocks are constitutionally different, i.e., each of these blocks comprises constitutional units derived from different characteristic species of monomer or with different composition or sequence distribution of constitutional units.

For example, a diblock copolymer of polybutadiene and polystyrene is referred to as polybutadiene-block-polystyrene. Such a copolymer is referred to generically as an "AB block copolymer." Likewise, a triblock copolymer can be represented as "ABA." Other types of block polymers exist, such as multiblock copolymers of the (AB), type, ABC block polymers comprising three different blocks, and star block polymers, which have a central point with three or more arms, each of which is in the form of a block copolymer, usually of the AB type.

As used herein, a "graft copolymer" refers to a macromolecule comprising one or more species of block connected as side chains to a linear main chain, wherein the side chains comprise constitutional or configurational features that differ from those in the main chain.

A "branch point" refers to a point on a chain at which a branch is attached. A "branch," also referred to as a "side chain" or "pendant chain," is an oligomeric or polymeric offshoot from a macromolecule chain. An oligomeric branch can be termed a "short chain branch," whereas a polymeric branch can be termed a "long chain branch."

A "chain" refers to the whole or part of a macromolecule, an oligomer, or a block comprising a linear or branched sequence of constitutional units between two boundary constitutional units, wherein the two boundary constitutional units can comprise an end group, a branch point, or combinations thereof.

A "main chain" or "backbone" refers to a linear chain from which all other chains are regarded as being pendant.

An "end group" refers to a constitutional unit that comprises the extremity of a macromolecule or oligomer and, by definition, is attached to only one constitutional unit of a macromolecule or oligomer.

"Biocompatible" as used herein, generally refers to a material and any metabolites or degradation products thereof that are generally non-toxic to the recipient and do not cause any significant adverse effects to the recipient.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks. In some embodiments, the polymer can degrade in less than seven days, e.g., in a time period from about 12 hours or 1 day to about 6 days.

The term "hydrophilic" can refer to a group or molecule that dissolves or preferentially dissolves in water and/or aqueous solutions.

The term "hydrophobic" refers to groups or molecules that do not significantly dissolve in water and/or aqueous solutions and/or which preferentially dissolve in fats and/or non-aqueous solutions.

The term amphiphilic refers to a molecule or polymer that contains both hydrophilic and hydrophobic groups.

The terms "conjugate" and "conjugated" can refer to compositions that comprise at least two different chemical moieties or molecules (e.g., small molecules, polymers, proteins, etc.) bonded to one another, such as via ionic, coordinative or covalent bonds. In some embodiments, the term "conjugate" refers to moieties or molecules that are covalently bonded to one another. In some embodiments, the conjugate can comprise two different chemical moieties associated with one another via intermolecular forces such as hydrogen bonding, London dispersion forces, van der Waals' interactions, $\pi$-$\pi$ stacking, etc.

The term "cancer" as used herein refers to diseases caused by uncontrolled cell division and the ability of cells to metastasize, or to establish new growth in additional sites. The terms "malignant", "malignancy", "neoplasm", "tumor" and variations thereof refer to cancerous cells or groups of cancerous cells. In some embodiments, the presently disclosed methods and compositions can be used to treat neoplasms. In some embodiments, the presently disclosed methods and compositions can cause apoptosis of malignant cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

As used herein the term "chemotherapy" refers to treatment with a cytotoxic compound (e.g., a DNA damaging compound) to reduce or eliminate the growth or proliferation of undesirable cells, such as, but not limited to, cancer cells. Thus, as used herein, "chemotherapeutic compound" and "chemotherapeutic agent" refer to a cytotoxic compound used to treat cancer. The cytotoxic effect of compound can be the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect.

Thus, chemotherapeutic agents include, but are not limited to, DNA damaging compounds and other chemicals that can kill cells. "DNA damaging compounds" include, but are not limited to, alkylating agents, DNA intercalators, protein synthesis inhibitors, inhibitors of DNA or RNA synthesis, DNA base analogs, topoisomerase inhibitors, and telomerase inhibitors or telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, Z-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, include alkylating agents such as dimethyl sulfate, mitomycin C, nitrogen and sulfur mustards; intercalating agents, such as acridine dyes, actinomycins, adriamycin, anthracenes, benzopyrene, ethidium bromide, propidium diiodide-intertwining; and other agents, such as distamycin and netropsin. Topoisomerase inhibitors, such as irinotecan, topotecan, camptothecin, lamellarin D, etoposide, teniposide, doxorubidin, daunorubicin, mitoxantrone, amsacrine, ellipticines, aurintricarboxylic acid, HU-331, coumermycin, nalidixic acid, novobiocin, and oxolinic acid; inhibitors of cell division, including colcemide, colchicine, vinblastine, and vincristine; and RNA synthesis inhibitors, including actinomycin D, a-amanitine and other fungal amatoxins, cordycepin (3'-deoxyadenosine), dichlororibofuranosyl benzimidazole, rifampicine, streptovaricin, and streptolydigin also can be used as chemotherapeutic agents.

Generally, the term "treating" refers to reducing or alleviating the symptoms or effects of a condition, disease, disorder, or injury, to any degree. Thus, "treating" can refer to methods of reducing or decreasing the effects of a condition, such that the effects of the condition or injury are of a lesser magnitude or shorter duration than the effects that would have occurred in the absence of the treating, as well as, in some embodiments, to methods of completely keeping one or more effects from occurring and/or continuing. For example, "treating" a cancer can involve reducing the size of a tumor, preventing or reducing the metastasis of a cancer to other sites in the body of the subject being treated; and/or to increasing the life span of the subject with a cancer.

II. Graft Copolymer Drug Conjugates and Nanocarriers

The presently disclosed subject matter provides, in some embodiments, a graft copolymer with pendant drug-containing segments. The pendant drug-containing segments can be oligomeric or polymeric. In some embodiments, the drug can be part of the monomer used to prepare the drug-containing polymeric or oligomeric segment, thereby providing that each pendant segment can contain multiple copies of a drug. Thus, in some embodiments, the graft copolymer is capable of high drug loading.

In some embodiments, the graft copolymer is biocompatible and/or biodegradable. For example, the drug can be covalently attached to the pendant segments via an ester linkage or other linkage that can be degraded under physiological conditions, thereby releasing the drug. Other components of the graft copolymer can also be biocompatible and/or biodegradable.

In some embodiments, the graft copolymer can form a nanoparticle or polymeric nanomicelle. For example, in some embodiments, the graft copolymer can fold (e.g., under aqueous conditions) into a polymeric nanomicelle in a protein refolding-like process (e.g., with hydrophilic portions of the copolymer on the outer surface of the micelle and hydrophobic portions, such as drug-containing graft segments, in the core/interior of the micelle).

In some embodiments, the nanomicelle can include at least two therapeutic drugs. In some embodiments, the second therapeutic drug is non-covalently encapsulated in the core of the nanomicelle. Thus, in some embodiments, the presently disclosed subject matter provides a nanoparticle/nanocarrier by folding a graft copolymer for dual drug delivery. Accordingly, in some embodiments, the presently disclosed subject matter provides a facile platform for combinational therapy (e.g., for treating cancer, inflammation, viral or other infection). In some embodiments, the nanoparticle can provide a temporal release of at least two drugs at different speeds. For example, in some embodiments, the graft copolymer is constructed by directly polymerizing a camptothecin-glutamate N-carboxyanhydride (Glu (CPT)-NCA) on multiple sites of a polyethylene glycol (PEG)-containing main chain via ring opening polymerization (ROP). In some embodiments, a drug encapsulated in a micelle of the graft copolymer (e.g., encapsulated doxorubicin) can be released relatively quickly, while a drug covalently conjugated to the graft copolymer of the micelle (e.g., camptothecin) can be released in a sustained manner.

Accordingly, in some embodiments, the presently disclosed subject matter provides a graft copolymer drug conjugate wherein the graft copolymer drug conjugate comprises a linear main chain and a plurality of polymeric side chains, wherein each polymeric side chain comprises a plurality of at least a first therapeutic agent covalently attached thereto. The linear main chain can be a homopolymer or a copolymer. In some embodiments, the linear main chain is copolymeric. The copolymeric main chain can comprise segments of one or more hydrophilic polymers and segments that contain branch points to which the drug-containing segments can be attached. Thus, in some embodiments, the linear main chain is a copolymer constructed from the polymerization of at least two monomers, one of which includes an attachment point for the drug-containing segments. Thus, one of the monomers, can act as a "tee-joint" and three reactive groups. Alternatively, the "tee-joint" monomer can comprise three reactive groups, but contain a masked or protected third reactive site that can be deprotected or unmasked prior to polymerization of the linear main chain copolymer with a third monomer.

In some embodiments, each polymeric side chain comprises a plurality of first therapeutic agent-containing monomeric units, wherein each of said first therapeutic agent-containing monomeric units comprises a divalent chemical moiety further comprising a covalently attached first therapeutic agent. In some embodiments, the first therapeutic agent is covalently attached via a linkage that can be enzymatically cleaved and/or that can be cleaved under physiological conditions at a desired location in vivo. For example, the linkage can be cleavable at a particular pH or via enzymes. In some embodiments, the linkage can be an ester or other linkage that can be cleaved by an intracellular esterase.

The first therapeutic agent can be any desirable therapeutic agent. In some embodiments, the first therapeutic agent can be selected from the group including, but not limited to, a chemotherapeutic agent, an anti-viral agent, an anti-inflammatory agent, an analgesic agent, an anesthetic, an antifungal agent, an antibiotic, an antihypertensive, an antimicrobial, an antipyretic, a cardioactive agent, a vasoconstrictor, a vasodilator, a nutritional supplement, a antiarthritic, a diuretic, a hormone, a radiation sensitizer, a sedative, a metal nanorod, and a therapeutic biological agent, such as a peptide or small interfering RNA (siRNA). In some embodiments, the first therapeutic agent is hydrophobic.

In some embodiments, the first therapeutic agent is a chemotherapeutic agent. Chemotherapeutic agents include, but are not limited to, DNA damaging compounds and other chemicals that can kill cells. Thus, chemotherapeutic agents include, but are not limited to, alkylating agents, DNA intercalators, protein synthesis inhibitors, inhibitors of DNA or RNA synthesis, DNA base analogs, topoisomerase inhibitors, and telomerase inhibitors or telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, include alkylating agents such as dimethyl sulfate, mitomycin C, nitrogen and sulfur mustards; intercalating agents, such as acridine dyes, actinomycins, adriamycin, anthracenes, benzopyrene, ethidium bromide, propidium diiodide-intertwining; and other agents, such as distamycin and netropsin. Topoisomerase inhibitors, such as irinotecan, topotecan, camptothecin, lamellarin D, etoposide, teniposide, doxorubidin, daunorubicin, mitoxantrone, amsacrine, ellipticines, aurintricarboxylic acid, HU-331, coumermycin, nalidixic acid, novobiocin, and oxolinic acid; inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as chemotherapeutic agents.

In some embodiments the first therapeutic agent is a topoisomerase inhibitor. In some embodiments, the first therapeutic agent is camptothecin.

In some embodiments, the graft copolymer drug conjugate can have the formula:

wherein:
A is a trivalent moiety;
B comprises a hydrophilic polymeric moiety;
X is a divalent moiety comprising a covalently attached first therapeutic agent;
n is an integer between 4 and 25;
m is an integer between 5 and 30; and
each of $R_1$, $R_2$, and $R_3$ is a monovalent moiety.

In some embodiments, A is derived from a trifunctional monomer comprising three chemically reactive functional groups wherein each of the three functional groups is independently selected from the group including, but not limited to, hydroxyl, amino, thiol, alkyl or aryl disulfide, isothiocyanate, thiocarbonylimidazole, thiocarbonylchloride, aldehyde, ketone, carboxylic acid, carboxylic acid ester, sulfonic acid, sulfonic acid ester, sulfonyl chloride, phosphoric acid, alkyl or aryl succinimidyl carbonate, alkyl or aryl chlorocarbonate, alkyl or aryl succinimidylthiocarbonate, alkyl or aryl chlorothiocarbonate, halide, and thioester. In some embodiments, A is derived from a natural or non-natural amino acid. In some embodiments, A is derived from a polyamine, such as a tris(aminoalkyl)amine or another amine that contains three primary amino groups. In some embodiments, the tris(aminoalkyl)amine is tris(aminoethyl)amine.

Any suitable hydrophilic polymeric moiety or moieties can be used as B. In some embodiments, the hydrophilic moiety is biocompatible and/or biodegradable. The hydrophilic polymeric moiety can have any suitable average molecular weight, e.g., between about 400 and about 10,000 (i.e., about 400, 500, 600, 700, 800, 900, 1000, 1250, 1500, 2000, 2500, 5000, 7500, or about 10000). Suitable hydrophilic polymeric moieties include, but are not limited to, poly(alkylene glycol), poly(vinyl alcohol), poly(2-hydroxyethyl methacrylate), poly[N-(2-hydroxypropyl)methacrylamide] (PHPMA), poly(acrylic acid), poly(methacrylic acid), poly(maleic acid), polylysine, dextran, chitosan, alginate, hyaluronic acid, and combinations thereof. In some embodiments, B is or comprises a poly(ethylene glycol) (PEG), such as $PE_{400}$, $PEG_{500}$, $PEG_{750}$, $PEG_{1000}$, $PEG_{1200}$, $PEG_{1500}$, $PEG_{2500}$, $PEG_{5000}$, and the like.

In some embodiments, X is derived from a monomer that comprises a moiety that can undergo ring opening polymerization (ROP). In some embodiments, the moiety that can undergo ring opening polymerization is a cyclic moiety that comprises one or more heteroatoms. The heteroatom-containing cyclic moiety can be selected from the group including, but not limited to, an epoxide, an aziridine, an episulfide, a lactone, a lactam, or a cyclic anhydride. In some embodiments, X is derived from a monomer comprising a N-carboxyanhydride (NCA) derived from a natural or non-natural amino acid. During ROP, the NCA can be opened by attack of a nucleophile (e.g., an amine) at the carbon atom of a carboxyl group. An amide linkage is formed, carbon dioxide can be released, and a new amine is formed from the nitrogen atom of the NCA. This nitrogen atom can react with another NCA group. Thus, ROP of NCAs can result in the formation of a polyamide.

In some embodiments, the amino acid is a conjugate of an amino acid and the first therapeutic agent. For example, the first therapeutic agent can be covalently attached to the amino acid via a linkage with a functional group on the amino acid side chain. In some embodiments, the amino acid side chain includes a carboxylic acid group that can form an ester linkage with a hydroxyl group on the first therapeutic agent. In some embodiments, the amino acid side chain can include a hydroxyl or thiol group that can form an ester or thioester with a carboxylic acid group on the first therapeutic agent. In some embodiments, the amino acid is glutamic acid or aspartic acid. In some embodiments, the amino acid-first therapeutic agent conjugate is glutamic acid covalently attached to the first therapeutic agent via the carboxylic acid side chain.

The monovalent moieties, $R_1$, $R_2$, and $R_3$ can be any suitable group. For example, each of $R_1$, $R_2$, and $R_3$ is independently selected from the group including, but not limited to, H, OH, $NH_2$, alkyl, aralkyl, aryl, acyl, a hydroxy protecting group, an amino protecting group (e.g., carbamates, such as a carbamate comprising t-butoxycarbonyl (BOC), fluorenylmethylcarbonyl (FMOC), or benzylcarbonyl (CBZ), an amides, such as acetamide or trifluoroacetamide, or a benzyl group (Bn)), and a fluorescent label or other detectable group (e.g., a radiolabel).

In some embodiments, the graft copolymer drug conjugate has the formula:

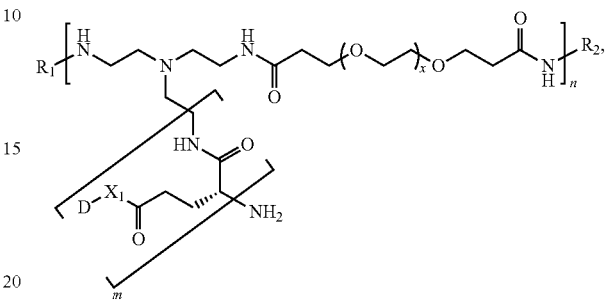

wherein:
n is an integer between 4 and 25;
m is an integer between 5 and 30;
x is an integer between 10 and 200;
$X_1$ is O, S, or NH;
D is a monovalent moiety derived from the first therapeutic agent; and
$R_1$ and $R_2$ are each monovalent moieties.

In some embodiments, x is 112. In some embodiments, the graft copolymer can have the structure shown in FIG. 1B.

In some embodiments, the graft copolymer drug conjugate can comprise between about 10 and about 30 weight percentage (%) of the first therapeutic agent (e.g., about 10, 12, 14, 16, 18, 20, 22, 24, 26, 28, or about 30 weight % of the first therapeutic agent). In some embodiments, the graft copolymer drug conjugate comprises between about 15 and about 25 weight % of the first therapeutic agent (e.g., about 15, 16, 17, 18, 19, 20, 21, 22, 23, 24, or about 25 weight % of the first therapeutic agent).

In some embodiments, the graft copolymer drug conjugate has a mass average molecular mass ($M_w$) between about 30,000 g/mol and about 40,000 g/mol (e.g., about 30,000; 31,000; 32,000; 33,000; 34,000; 35,000; 36,000; 37,000; 38,000; 39,000; or about 40,000 g/mol).

When the first therapeutic agent is a hydrophobic compound (e.g., such as camptothecin), the graft copolymer can fold into a micelle in aqueous solution. In some embodiments, the presently disclosed graft copolymer drug conjugates can have a critical micelle concentration (CMC) between about 0.002 mg/ml and about 0.003 mg/mL (e.g., about 0.0020, 0.0021, 0.0022, 0.0023, 0.0024, 0.0025, 0.0026, 0.0027, 0.0028, 0.0029, or about 0.0030 mg/mL. In some embodiments, the CMC is between about 0.0023 mg/mL and about 0.0025 mg/mL.

Accordingly, in some embodiments, the presently disclosed subject matter provides a polymeric micelle comprising a graft copolymer drug conjugate. In some embodiments, the polymeric micelle can comprise at least one therapeutic agent covalently attached to the graft copolymer of the micelle and at least one therapeutic agent (e.g., a second therapeutic agent) encapsulated non-covalently within the micelle. For instance, when exposed to water or another aqueous solution together with a free second therapeutic agent, the presently disclosed graft copolymer drug conjugate can form a micelle for dual drug delivery of the first and second therapeutic agents. Coordination of the solubility, pharmacokinetics and biodistribution of multiple drugs by the presently disclosed micelles can be used to overcome problems commonly associated with traditional drug "cocktail" methodology.

The second therapeutic agent can be any suitable type of agent, such as, but not limited to, a chemotherapeutic agent, an anti-viral agent, an anti-inflammatory agent, an analgesic agent, an anesthetic, an antifungal agent, an antibiotic, an antihypertensive, an antimicrobial, an antipyretic, a cardioactive agent, a vasoconstrictor, a vasodilator, a nutritional supplement, a antiarthritic, a diuretic, a hormone, a radiation sensitizer, a sedative, a metal nanorod, and a therapeutic biological agent, such as a peptide or small interfering RNA (siRNA). In some embodiments, such as when the first therapeutic agent is a chemotherapeutic agent, the second chemotherapeutic agent can be an agent that treats a side effect of the first agent. In some embodiments, both the first and second therapeutic agents are chemotherapeutic agents. The two chemotherapeutic agents can have different mechanisms of action and/or molecular targets.

Topoisomerase (Top) represents a popular target in cancer chemotherapy. Its inhibitors can block the DNA ligation step during cell cycling, and induce irreversible single and double stranded DNA breaks during transcription and replication, thereby leading to apoptosis and cell death. See Binaschi et al., Stem Cells, 13, 369-379 (1995). Both CPT and Dox are potent Top inhibitors, but they interfere with the action of Top I and II, respectively. CPT as a Top I inhibitor has shown potent anti-tumor efficiency in a broad spectra of cancers in clinic. See Wall et al., Ann. N.Y. Acad. Sci., 803, 1-12 (1996); and Wall et al., Cancer Res., 55, 753-760 (1995). However, certain clinical limitations such as resistance of cancer cells can impair its clinical application. See Beretta et al., Curr. Med. Chem., 13, 3291-3305 (2006); and Saleem et al., Ann. N.Y. Acad. Sci., 922, 46-55 (2000). It has been postulated that reduced Top I activity following the CPT treatment could be compensated by Top II, because the actions of both enzymes are partially overlapping. See Tan et al., J. Natl. Cancer Inst., 81, 1732-1735 (1989).

In some embodiments, the first and second therapeutic agents are both Top inhibitors. In some embodiments, one of the first and second therapeutic agents inhibits Top I and the other of the first and second therapeutic agents inhibits Top II. In some embodiments, the first therapeutic agent inhibits Top I and the second therapeutic agent inhibits Top II. In some embodiments, the first therapeutic agent is CPT and the second therapeutic agent is Dox. In such embodiments, the Dox can be released relatively rapidly in vivo, while the CPT can be released in a sustained manner.

In some embodiments, the polymeric micelle of the presently disclosed subject matter comprises up to about 30 weight % of the second therapeutic agent (i.e., compared to the weight of graft copolymer drug conjugate). For example, the micelle can comprise about 5, 7.5, 10, 12.5, 15, 17.5, 20, 22.5, 25, 27.5, or about 30 weight % of the second therapeutic agent. In some embodiments, the micelle can comprise about 10 weight % of the second therapeutic agent.

In some embodiments, the micelle can have an average diameter of about 250 nm or less (e.g., about 250, about 225, about 200, about 175, about 150, or about 125 nm or less). In some embodiments, the micelle can have an average diameter between about 10 nm and about 100 nm (e.g., about 10, 20, 30, 40, 50, 60, 70, 80, 90, or about 100 nm). In some embodiments, the micelle can have an average diameter of between about 25 nm and about 75 nm. In some embodiments, the micelle can have an average diameter of between about 50 nm and about 70 nm.

In some embodiments, the polymeric micelles can have a particle size polydispersity index (PDI) that is about 0.2 or less. In some embodiments, the PDI is between about 0.1 and about 0.2 (e.g., about 0.10, 0.11, 0.12, 0.13, 0.14, 0.15, 0.16, 0.17, 0.18, 0.19, or about 0.2). In some embodiments, the PDI is between about 0.13 and about 0.17.

III. Pharmaceutical Compositions

In some embodiments, the presently disclosed subject matter provides a pharmaceutical composition comprising a graft copolymer drug conjugate as described hereinabove or a micelle thereof. In addition to the graft copolymer drug conjugate or micelle thereof, the pharmaceutical composition can further include a pharmaceutically acceptable carrier. In some embodiments, the presently disclosed pharmaceutical compositions can provide delivery of two of more (e.g., two, three, four or more) therapeutic agents. The two or more therapeutic agents can have different release profiles and/or be used to treat or prevent the same or different diseases. In embodiments wherein the polymeric micelle comprises a covalently attached first therapeutic agent and an encapsulated second therapeutic agent, the second therapeutic agent can have a rapid release profile and the first therapeutic agent can have a sustained release profile.

As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the liposomal pharmaceutical compositions. The presently disclosed compositions can be lyophilized to produce a lyophilizate, which can be reconstituted with a pharmaceutically acceptable carrier, such as water, to regenerate a suspension or solution.

Therapeutic agents encapsulated in the presently disclosed micelles and/or added to pharmaceutical compositions of micelles can be present in a salt form. Pharmaceutically acceptable salts include, but are not limited to, gluconate, lactate, acetate, tartarate, citrate, phosphate, maleate, borate, nitrate, sulfate, and hydrochloride salts. For additional salt forms, see, for example, Berge et al., J. Pharm. Sci., 66, 1-19 (1977). The salts can be prepared, for example, by reacting the base compound with the desired acid in solution. After the reaction is complete, the salts are crystallized from solution by the addition of an appropriate amount of solvent in which the salt is insoluble.

A pharmaceutical composition can be formulated to be compatible with its intended route of administration. Examples of routes of administration include, but are not limited to, parenteral, intravenous, intradermal, subcutaneous, oral (e.g., inhalation), transdermal (topical), transmucosal, nasal, optical, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Oral compositions generally include an inert diluent or an edible carrier. For the purpose of oral therapeutic administration, the compositions can include excipients and be used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions or dispersions and sterile powders for the extemporaneous preparation of sterile injectable solutions or dispersion. For intravenous administration, suitable carriers include, but are not limited to, physiological saline, bacteriostatic water, PEGylated Castor oil, or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, other fluids configured to preserve the integrity of the micelle, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols such as mannitol, sorbitol, and sodium chloride sometimes are included in the composition. Prolonged absorption of the injectable compositions can be brought about by including in the composition an agent which delays absorption, for example, aluminum monostearate and gelatin. Sterile injectable solutions can be prepared by incorporating the micelles in the required amount in an appropriate solvent with one or a combination of ingredients enumerated above, as required, followed by filtered sterilization.

For administration by inhalation, the compositions can be delivered in the form of an aerosol spray from pressured container or dispenser that contains a suitable propellant, e.g., a gas such as carbon dioxide, or a nebulizer.

Systemic administration can also be by transmucosal or transdermal means, including nasal and optical. For transmucosal or transdermal administration, penetrants appropriate to the barrier to be permeated are used in the compositions. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compositions can be formulated into ointments, salves, gels, or creams as generally known in the art. Compositions can also be prepared in the form of suppositories (e.g., with conventional suppository bases such as cocoa butter and other glycerides) or retention enemas for rectal delivery.

In some embodiments oral or parenteral compositions are formulated in a dosage unit form for ease of administration and uniformity of dosage. Dosage unit form as used herein refers to physically discrete units suited as unitary dosages for the subject to be treated; each unit containing a predetermined quantity of therapeutic agents or micelles calculated to produce the desired therapeutic effect in association with the required pharmaceutical carrier.

Toxicity and therapeutic efficacy of the presently disclosed compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In some embodiments, micelle delivery can increase the therapeutic index of one or more therapeutic agents (e.g., by increasing $LD_{50}$).

The data obtained from the cell culture assays and animal studies can be used in formulating a range of dosage for use in humans or another species. The dosage can lie within a range of circulating concentrations that include the $ED_{50}$ with little or no toxicity. The dosage can vary within this range depending upon the dosage form employed and the route of administration utilized. The therapeutically effective dose can be estimated initially from cell culture assays. A dose may be formulated in animal models to achieve a circulating plasma concentration range that includes the $IC_{50}$ (i.e., the concentration of the micelles or individual therapeutic agents therein which achieves a half-maximal inhibition of symptoms) as determined in cell culture. Such information can be used to more accurately determine useful doses in humans.

IV. Methods of Treating Disease

In some embodiments, the presently disclosed subject matter provides a method of treating a disease in a subject in need thereof. In some embodiments, the method comprises administering to the subject a graft copolymer drug conjugate of the presently disclosed subject matter. In some embodiments, the method comprises administering to the subject a micelle formed from a graft copolymer drug conjugate. In some embodiments, the method comprises administering to the subject a pharmaceutical composition comprising a graft copolymer drug conjugate and/or micelle thereof.

The subject treated in the presently disclosed subject matter in its many embodiments is desirably a human subject, although it is to be understood the methods described herein are effective with respect to all vertebrate species, which are intended to be included in the term "subject." In some embodiments, the subject is a warm-blooded vertebrate.

More particularly, provided herein is the treatment of mammals, such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos or as pets (e.g., parrots), as well as fowl, and more particularly domesticated fowl, i.e., poultry, such as turkeys, chickens, ducks, geese, guinea fowl, and the like, as they also are of economic importance to humans. Thus, embodiments of the methods described herein include the treatment of livestock, including, but not limited to, domesticated swine (pigs and hogs), ruminants, horses, poultry, and the like. In some embodiments, the subject is a human or a dog.

The graft copolymer drug conjugate, micelle, and/or pharmaceutical composition thereof can be administered to the subject via any convenient route. In accordance with the presently disclosed methods, the graft copolymer drug conjugate, micelle and/or pharmaceutical composition thereof can be provided to a subject via topical (e.g., directly to a site of disease, such as directly to a tumor or site of infection), enteral, or parenteral administration. In some embodiments, the graft copolymer drug conjugate, micelle, and/or pharmaceutical composition thereof is administered orally (e.g., as a solid or as a liquid), or can be administered intramuscularly, intravenously, rectally, sublingually, via buccal administration, via intraperitoneal administration, via intrathecal administration, intraocular administration, or by inhalation (e.g., as a solution, suspension, or emulsion). In some embodiments, the graft copolymer drug conjugate, micelle, and/or pharmaceutical composition thereof is administered intravenously.

The disease to be treated or prevented can be any disease treatable by a therapeutic agent that can be incorporated into the presently disclosed graft copolymer drug conjugate and/or micelle. The disease to be treated or prevented can be selected from the group including, but not limited to, cancer, an inflammatory disease (e.g., arthritis), hypertension, heart disease, and a viral or other infection (e.g., a fungal or bacterial infection).

In some embodiments, the disease is cancer. The cancer can be selected from skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers. In some embodiments, the cancer is selected from breast cancer, lung cancer, liver cancer, prostate cancer, cervical cancer, and leukemia. In some embodiments, the cancer is lung cancer.

In some embodiments, the method comprises administering to a subject in need thereof a micelle as presently disclosed herein or a pharmaceutical composition thereof, wherein the micelle comprises a second therapeutic agent encapsulated within the micelle (i.e., in addition to the first therapeutic agent attached (e.g., covalently attached) to the polymeric side chains of the graft copolymer drug conjugate). Thus the presently disclosed methods can comprise treatment with a plurality (e.g., two, three, four, five or more) of therapeutic agents. One of the plurality of therapeutic agents can be used to treat the disease, while another of the plurality of therapeutic agents can be used to treat a side effect of one of the therapeutic agents (e.g., nausea) or to treat a second disease of condition. In some embodiments, the micelle can also comprise (e.g., in addition to the first therapeutic agent or in addition to the first and second therapeutic agents) an agent to track administration of the micelle, such as a fluorescent agent or other detectable agent.

In some embodiments, the first and second therapeutic agents are both chemotherapeutic agents. Thus, the presently disclosed methods can relate to combinatorial chemotherapy. In some embodiments, the micelle preferentially accumulates in cancer cells, e.g., as compared to non-cancer cells, such as non-cancerous heart, spleen and/or kidney cells. In some embodiments, the first and second chemotherapeutic agents can have different mechanisms of action and/or molecular targets. In some embodiments, the first and second chemotherapeutic agents have synergistic effects.

In some embodiments, the first and second chemotherapeutic agents are both topoisomerase inhibitors, such as, but not limited to, irinotecan, topotecan, camptothecin, lamellarin D, etoposide, teniposide, doxorubidin, daunorubicin, mitoxantrone, amsacrine, ellipticines, aurintricarboxylic acid, HU-331, coumermycin, nalidixic acid, novobiocin, and oxolinic acid. In some embodiments, one of the chemotherapeutic agents inhibits Top I and the other inhibits Top II. In some embodiments, the Top I inhibitor is selected from, for example, irinotecan, topotecan, camptothecin, and lamellarin D. In some embodiments, the Top II inhibitor is selected from, for example, etoposide, teniposide, doxorubidin, daunorubicin, mitoxantrone, amsacrine, ellipticines, aurintricarboxylic acid and HU-331. In some embodiments, the first chemotherapeutic agent is a Top I inhibitor and the second chemotherapeutic agent is a Top II inhibitor. In some embodiments, the first chemotherapeutic agent is camptothecin and the second chemotherapeutic agent is doxorubicin.

In some embodiments, the presently disclosed methods can be used in conjunction with other treatments, e.g., radiation and/or surgery. In some embodiments, the presently disclosed methods can comprise administering the graft copolymer drug conjugate, micelle, and/or pharmaceutical composition to the subject in need thereof a plurality of times. The administration schedule can vary from patient to patient and depend upon the therapeutic agents used, the dose, the type and severity of the cancer or disease, etc.

V. Methods of Preparing Graft Copolymer Drug Conjugates and Micelles

Figure 1B:
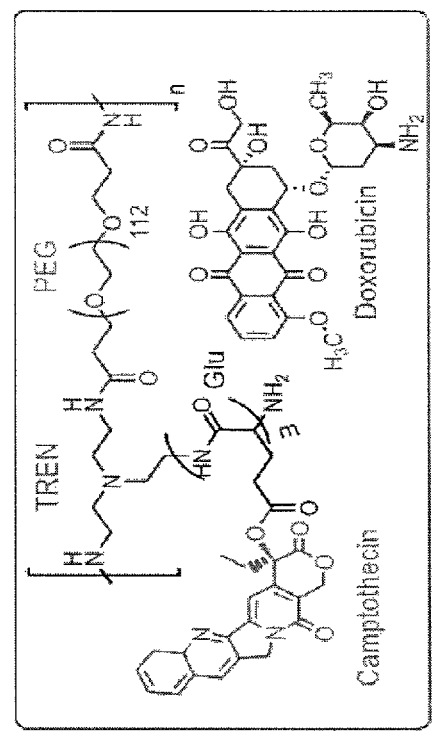
FIG. 1B is a schematic drawing showing the chemical structure of a graft copolymer of the presently disclosed subject matter, such as a graft copolymer as described for FIG. 1A, side-by-side with the chemical structure of doxorubicin. The graft copolymer comprises repeating blocks of poly(ethylene glycol) (PEG) and tris(aminoethyl)amine (TREN), with graft segments comprising a polymer of a camptothecin-modified glutamic acid (Glu).

In some embodiments, the presently disclosed subject matter provides a method of preparing a graft copolymer drug conjugate. For instance, in some embodiments, the method can comprise a two-step polymerization as illustrated in FIG. 1A. The first step can comprise the polymerization of two monomers, e.g., monomer I and monomer II of Figure IA, to form a linear copolymer. One of the monomers, monomer I can comprise a site that can serve as the point of attachment for polymeric graft segments during the second step. Thus, monomer I can serve as a "tee-joint" for the graft copolymer. The site of attachment for the graft segments on monomer I can optionally be masked or protected during the first step polymerization. The second step can comprise polymerization (e.g. ring-opening polymerization) of a third monomer, e.g., monomer III of FIG. 1A, to provide polymeric graft segments.

In some embodiments, monomer III can comprise at least a first therapeutic agent. In some embodiments, this first therapeutic agent can be covalently attached to monomer Ill. Accordingly, each of the plurality of graft segments of the final graft copolymer can comprise a plurality of the at least first therapeutic agent. Further, unlike preparations wherein a therapeutic agent is attached to a polymer following polymerization, the direct polymerization of the first therapeutic agent (i.e., the presence of the first therapeutic agent in monomer III) can result in 100% drug conjugation in the side chains (e.g., no side chains are formed without the presence of a therapeutic agent).

The presently disclosed graft copolymers can present a well-controlled architecture and relatively narrow distributed molecular weight. Further, the content of first therapeutic agent in the graft copolymer can be easily tuned by the side-chain length, which is controlled by the feed ratios of linear polymer and monomer III during the second-step polymerization.

In some embodiments, the presently disclosed subject matter provides a method of preparing a graft copolymer drug conjugate as described hereinabove, wherein the method comprises: (a) contacting a first monomer and a second monomer in a first solvent to provide a linear copolymer, wherein the first monomer comprises a partially protected trifunctional compound, wherein the partially protected trifunctional compound comprises three chemically reactive groups, wherein each of said chemically reactive groups can be the same or different and wherein one of said three chemically reactive groups is protected with a protecting group, and wherein the second monomer is a bifunctional derivative of a hydrophilic polymer; (b) contacting the linear copolymer with a deprotecting reagent to remove the protecting group, thereby providing a deprotected linear copolymer; and (c) contacting the deprotected linear copolymer with a third monomer in a second solvent, wherein the third monomer comprises a polymerizable group and a covalently attached first therapeutic agent, thereby providing a graft copolymer comprising a plurality of first therapeutic agents.

The chemically reactive groups of the first monomer and the functional derivative groups of the bifunctional derivative can be any suitable groups. In some embodiments, the chemically reactive groups or functional derivative groups can be selected from the group including, but not limited to, hydroxyl, amino, thiol, alkyl or aryl disulfide, isothiocyanate, thiocarbonylimidazole, thiocarbonylchloride, aldehyde, ketone, carboxylic acid, carboxylic acid ester, sulfonic acid, sulfonic acid ester, sulfonyl chloride, phosphoric acid, alkyl or aryl succinimidyl carbonate, alkyl or aryl chlorocarbonate, alkyl or aryl succinimidylthiocarbonate, alkyl or aryl chlorothiocarbonate, halide, and thioester.

In some embodiments, the second monomer comprises a hydrophilic polymer comprising two activated esters. Activated esters can be prepared from esterification of a carboxylic acid with an alcohol comprising an electronegative group, such as, but not limited to, a halo-substituted phenol (e.g., pentafluorophenol, 2,4,6-trichlorophenol, 2,4,5-trichlorophenol, pentachlorophenol), para-nitrophenol, 8-hydroxyquinoline, 3-hydroxypyridine, and N-hydroxysuccinimide. For instance, in some embodiments, the second monomer is a PEG comprising two activated esters, such as N-hydroxysuccinimide esters, which can be the same or different. In some embodiments, the second monomer is a bis-N-hydroxysuccinimide ester $PEG_{500}$.

In some embodiments, the polymerizable group of the third monomer can undergo ring opening polymerization. Thus, in some embodiments, the third monomer can comprise a cyclic moiety that comprises a heteroatom (e.g., an epoxide, an aziridine, an episulfide, a lactone, a lactam, or a cyclic anhydride). In some embodiments, the third monomer is a N-carboxyanhydride (NCA) derived from an amino acid-first therapeutic agent conjugate. For instance, the amino acid-first therapeutic agent can comprise a first therapeutic agent attached to an amino acid via a covalent linkage with a functional group on the amino acid side chain and the NCA is formed from atoms of the amino and carboxylic acid groups of the amino acid. In some embodiments, the amino acid side chain includes a carboxylic acid group that can form an ester linkage with a hydroxyl group on the first therapeutic agent. In some embodiments, the amino acid side chain can include a hydroxyl or thiol group that can form an ester or thioester with a carboxylic acid group on the first therapeutic agent. In some embodiments, the amino acid is glutamic acid or aspartic acid. In some embodiments, the amino acid-first therapeutic agent conjugate is glutamic acid covalently attached to the first therapeutic agent via the carboxylic acid side chain.

In some embodiments, the first monomer is a mono-protected polyamine, such as, but not limited to a mono-protected tris(aminoalkyl)amine. Any suitable amino protecting group known in the art can be used, such as, but not limited to a carbamate (e.g., BOC or FMOC). The protecting group can be removed by methods known in the art. For example, when the protecting group is BOC, the protecting group can be removed with trifluoroacetic acid (TFA) in a non-polar solvent. In some embodiments, the first monomer is N,N-bis(2-aminoethyl)-N-[2-(tert-butylcarbamoyl)ethyl] amine.

In some embodiments, the first solvent is a polar, aprotic solvent, such as, but not limited to, acetone, acetonitrile, butanone, dimethylformamide (DMF), and dimethylsulfoxide (DMSO). In some embodiments, the first solvent is DMF.

In some embodiments, the second solvent is a non-polar solvent, such as, but not limited to, diethyl ether, an aliphatic hydrocarbon (e.g., pentane or hexane), an aromatic hydrocarbon (e.g., benzene or toluene), or a halogenated hydrocarbon (e.g., DCM or chloroform). In some embodiments, the second solvent is chloroform.

The first and second monomers can be contacted in any suitable molar ratio, e.g., to control the content of the linear copolymer and/or depending upon the relative reactivities of the monomers. In some embodiments, the first and second monomers are contacted in a 1/1 molar ratio in step (a).

In some embodiments, the method further comprises activating the deprotected linear copolymer prior to step c). In some embodiments, the activating comprises preparing a trimethylsilyl (TMS) derivative of a free amine in the deprotected linear copolymer. The activation can be performed by reacting the deprotected linear copolymer with N, O-bis(trimethylsilyl) acetamide (BSA) in a non-polar solvent, such as benzene.

As noted hereinabove, the loading of drug can be controlled by adjusting the feed ratio of linear polymer and third monomer during ROP. In some embodiments, step c) comprises contacting between about 5 and about 35 molar equivalents (e.g., about 5, 10, 15, 20, 25, 30 or 35 molar equivalents) of the third monomer with one molar equivalent of the linear copolymer (i.e., the deprotected linear copolymer). In some embodiments, about 20 equivalents of the third monomer are contacted with one molar equivalent of the linear copolymer.

In some embodiments, the presently disclosed subject matter further provides a method of preparing a micelle from a graft copolymer drug conjugate. Thus, in some embodiments, the presently disclosed subject matter provides a method of preparing a micelle comprising preparing a solution of a graft copolymer drug conjugate (such as the graft copolymer provided in step c) of the method above) in an organic solvent and mixing the solution with water. Once in water, the graft copolymer drug conjugate can fold to form a micelle (e.g., a nanomicelle). In some embodiments, e.g., wherein a second therapeutic agent is to be present within the micelle, preparing the solution of the graft copolymer in the organic solvent further comprises dissolving a second therapeutic agent in the solution, wherein when the solution is mixed with water, micelles are formed with the second therapeutic agent encapsulated therein. The loading of the second therapeutic agent can be controlled by varying the amount of second therapeutic agent added to the solution.

In some embodiments, the organic solvent is miscible with water. Thus, the organic solvent can be selected from the group comprising, but not limited to, acetone, DMF, acetonitrile, DMSO, and N-methylpyrrolidone (NMP). In some embodiments, the organic solvent is NMP.

The organic solvent can be removed, e.g., via dialysis. If desired, the micelle can be frozen and lyophilized for storage.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

General Methods and Materials

All chemicals were obtained from commercial sources and used without further purification. Tris(2-aminoethyl) amine, di-t-butyl dicarbonate ($Boc_2O$), trifluoroacetic acid (TFA), N,O-bis(trimethylsilyl) acetamide (BSA) and triphosgene were purchased from Sigma Aldrich (St. Louis, Missouri, United States of America). N,N'-diisopropylcarbodiimide (DIPC), triethylamine ($Et_3N$) and 4-dimethylaminopyridine (DMAP) were obtained from Acros Organics (Geel, Belgium). NHS-$PEG_{5000}$-NHS was purchased from Nanocs Inc. (New York, N.Y., United States of America). Camptothecin (CPT) and doxorubicin (Dox) were purchased from Alfa Aesar (Ward Hill, Massachusetts, United States of America). Boc-L-glutamic acid 5-tert-butyl ester (Boc-Glu-OtBu) was ordered from Chem-Impex International Inc. (Wood Dale, Ill., United States of America). All the organic solvents for synthesis and analysis were ordered from Fisher Scientific Inc. (Waltham, Mass., United States of America) and used as received.

Student's t-test or ANOVA were utilized to determine statistical significancebetween different groups. A p value <0.05 was considered to be statistically significant.

Example 2

Synthesis of Graft Copolymer

An exemplary graft copolymer 5 (i.e., the graft copolymer shown in FIG. 1B) of the presently disclosed subject matter was prepared as shown in FIG. 2A.

More particularly, monomer I of FIG. 2A, i.e., N,N-bis (2-aminoethyl)-N-[2-(tert-butylcarbamoyl)ethyl-amine (2), was synthesized as previously reported. See Boon et al., J. Org. Chem., 67, 2168-2174 (2002); and Benito et al., J. Am. Chem. Soc., 126, 10355-10363 (2004). Briefly, a chloroform solution of $Boc_2O$ (1 g, 4.6 mmol, 0.1 equiv) was added dropwise into a stirred solution of tris(2-aminoethyl)amine (1) (6.7 g, 46 mmol) in 300 mL of chloroform at 0° C. The reaction was allowed to warm to room temperature and stirred overnight. The reaction was stopped by 15 mL of DD water. After stirring for 5 min, the organic phase was separated. The aqueous phase was re-extracted with 30 mL of chloroform. The combined organic phase was dried with $Na_2SO_4$, then concentrated under vacuum to give crude compound 2 which was purified by silica gel chromatography using $CHCl_3$/MeOH/concentrated aqueous $NH_4OH$ (v/v/v, 10/5/1) as eluent. The purified monomer I (i.e., 2) was given as viscous oil (1.05 g, 92%). $^1H$ NMR (300 MHz, DMSO-$d_6$): δ 6.81 (t, 1H), 2.95 (q, 2H), 2.81 (brs, 4H), 2.52 (t, 4H), 2.38 (q, 6H), 1.39 (s, 9H). ESI-MS calcd for $C_{11}H_{26}N_4O_2$ 246.21, found 247.21 $[M+H]^+$.

Multiblock copolymer 3 of FIG. 2A was prepared as previously described. See Tai et al., Pharmaceutical Research, 1-14 (2013). Briefly, monomer I (2) and NHS-$PEG_{5000}$-NHS (monomer II) were dried in a $CaCl_2$ desiccator for two days before synthesis. One gram of NHS-$PEG_{5000}$-NHS (0.2 mmol, 1 equiv) was dissolved in 4 mL of dry DMF, followed by adding 0.5 mL of monomer I (52.1 mg, 0.2 mmol, 1equiv) solution in DMF at $N_2$ atmosphere. The reaction was initiated by adding 140 μL of dry $Et_3N$. Two days later, the reaction mixture was poured into 50 mL of diethyl ether. The precipitate was washed twice with diethyl ether, dried in vacuum and yielded as white powder (860 mg, 81%). $^1H$ NMR (300 MHz, $CDCl_3$): δ 4.21 (t, 2H), 3.63 (s, 448H), 3.17 (m, 4H), 2.55 (t, 6H), 2.37 (brs, 4H), 1.43 (s, 9H).

Referring again to FIG. 2A, to remove the BOC protecting group, polymer 3 was dissolved in 10 mL of dichloromethane (DCM) and TFA mixture (v/v, 1/1). A scavenger, phenol (140 mg), was also added into the mixture to minimize side reactions. The reaction mixture was stirred at room temperature for 1 h. The organic solvent was evaporated under vacuum and the residue was washed with diethyl ether. After removing the remaining organic solvent under vacuum, the residue was dissolved in water and dialyzed against distilled, deionized (DD) water with cellulose tubing (molecular weight cut off (MWCO): 12 kDa). The resulting solution was lyophilized and dried in $CaCl_2$ desiccator.

The amine groups on the deprotected linear multiblock copolymer were activated with TMS. The dry polymer (200 mg) was mixed with 5 mL of anhydrous benzene. After the polymer was completely dissolved, 2 mL of N,O-bis(trimethylsilyl) acetamide (BSA) was added. The reaction was stirred at room temperature for 24 h. Anhydrous hexane (20 mL) was added into the reaction mixture to precipitate the product. The white precipitate was washed three times with anhydrous hexane and dried under vacuum to give polymer 4 in quantitative yield. $^1H$ NMR (300 MHz, $CDCl_3$): δ 4.21 (t, 2H), 3.64 (s, 448H), 3.20 (m, 4H), 2.60 (m, 6H), 2.12 (m, 4H), 0.01 (s, 9H).

The ring-open polymerization of the side chains was initiated by N-TMS amines. See Lu et al., J. Am. Chem. Soc., 130, 12562-12563 (2008). Briefly, as shown in FIG. 2A, monomer III (121.1 mg; see synthesis below) and polymer 4 (62.1 mg) were suspended in 5 mL of dry chloroform. The yellow suspension gradually turned clear after adding 75 μL of dry $Et_3N$. The reaction gradually became turbid over time, indicating the successful polymerization. After 48 h, the reaction mixture was poured into 30 mL of diethyl ether to precipitate the product. After washing three times with diethyl ether, the precipitate was dried under vacuum to give graft copolymer 5. Graft polymerization can be facilitated by extensively washing polymer 4 prior to reaction with monomer Ill, as trace amounts of BSA in polymer 4 can induce side reactions, resulting in failure of graft polymerization and large aggregation during folding. Directly initiating graft polymerization with amine (the intermediate of polymer 4) is also applicable, but with less ROP efficiency. See Lu et al., J. Am. Chem. Soc., 130, 12562-12563 (2008). Graft copolymer 5: $^1H$ NMR (300 MHz, DMSO-$d_6$): δ 8.68 (s, 10H), 8.14 (m, 20H), 7.82 (m, 10H), 7.69 (m, 10H), 7.05 (s, 10H), 5.47 (m, 20H), 5.25 (br, 20H), 4.01 (s, 10H), 3.51 (s, 448H), 2.12 (br, 50H), 0.86 (br, 30H).

Example 3

Synthesis of Monomer III, Glu(CPT)-NCA

As shown in FIG. 2B, Boc-Glu(CPT)-OtBu was prepared as follows. To a suspension of camptothecin (CPT, 0.8 g) in chloroform (50 mL), Boc-Glu-OtBu (2.4 g), DIPC (2.4 mL) and DMAP (0.154 g) were separately added. The suspension was stirred at room temperature and the reaction gradually turned clear after around 1 h. The reaction was stopped by adding 30 mL of saturated $NH_4Cl$ aqueous solution. The organic phase was separated, washed with brine and dried by $Na_2SO_4$. The organic solvent was removed by evaporation under vacuum and the crude product was purified by silica gel chromatography eluted with hexane/EtOAc (v/v=2/1, then 1/1 and then EtOAc only). The pure product Boc-Glu (CPT)-OtBu was given as white powder with yield of 80%. $^1$H NMR (300 MHz, DMSO-$d_6$): δ 8.68 (s, 1H), 8.14 (t, 2H), 7.86 (t, 1H), 7.71 (t, 1H), 7.22 (d, 1H), 7.07 (s, 1H), 5.50 (s, 1H), 5.28 (s, 1H), 3.88 (m, 1H), 2.62 (m, 2H), 2.17 (t, 2H), 1.89 (q, 2H), 1.37 (s, 18H), 0.92 (t, 3H).ESI-MS calcd for $C_{34}H_{39}N_3O_9$ 633.28, found 634.27 $[M+H]^+$.

The compound Boc-Glu(CPT)-OtBu was dissolved in 10 mL of DCM at 0° C. TFA (10 mL) was then added into the reaction. The mixture was allowed to warm to room temperature and stirred for 1.5 h. The solvent was removed under vacuum and the product was then precipitated with diethyl ether. After washing three times with ether, the precipitate was dried under vacuum (yield, 90%). Glu(CPT)-OH $^1$H NMR (300 MHz, DMSO-$d_6$): δ 8.68 (s, 1H), 8.15 (t, 2H), 7.86 (t, 1H), 7.71 (t, 1H), 7.09 (s, 1H), 5.51 (s, 2H), 5.28 (s, 2H), 3.96 (t, 1H), 3.46 (brs, 2H), 2.76 (m, 2H), 2.16 (m, 2H), 2.05 (m, 2H), 0.93 (t, 3H). ESI-MS calcd for $C_{25}H_{23}N_3O_7$ 477.16, found 478.16 $[M+H]^+$.

Glu(CPT)-OH (280 mg) was added to 300 mL of anhydrous THF. The mixture was sonicated in an ultrasonic water tank for a couple minutes to disperse the Glu(CPT)-OH in THF. After adding triphosgene (170 mg), the suspension was stirred at 48° C. for 2 h. The suspension gradually became clear, indicating the completion of the reaction. The reaction was concentrated under vacuum and the yellow residue was re-dissolved in 15 mL of anhydrous THF. The crude product was precipitated with 30 mL of anhydrous hexane. The precipitate was collected by centrifuge, washed twice with anhydrous THF/hexane mixture (v/v, 1/2), and dried in the vacuum desiccators (yield, 70%). Glu(CPT)-NCA: $^1$H NMR (300 MHz, DMSO-$d_6$) δ 9.19 (s, 1H), 8.69 (s, 1H), 8.15 (t, 2H), 7.87 (t, 1H), 7.71 (t, 1H), 7.13 (s, 1H), 5.51 (s, 2H), 5.27 (s, 2H), 4.46 (m, 0.5H), 3.59 (m, 0.5H), 2.74 (t, 2H), 2.15 (q, 2H), 1.98 (m, 2H), 0.93 (t, 3H).

Example 4

Graft Copolymer Nanocarriers

Graft copolymer 5 from FIG. 2A was dissolved in N-methylpyrrolidone (NMP) to obtain a homogenous solution with concentration of 10 mg/mL. To obtain the MB-20 nanocarriers, 1 mL of the graft copolymer solution was added into 6 mL of DD water dropwise under vigorous stirring. The micelle solution was then sonicated for 20 cycles (1 s each with a duty cycle of 20%). The homogenous micelle solution was dialyzed against DD water for 24 h at room temperature to completely remove the organic solvent NMP. The DD water was frequently changed during the dialysis process. The nanocarrier solution was passed through 0.45 μm SFCA syringe filter (Corning Inc, Corning, N.Y., United States of America). The folded micelle was stored at 4° C. for further characterization. For long-term storage, 10 mL of micelle solution was mixed with 100 mg of cryoprotectant hydroxypropyl-β-cyclodextrin (HPβCD), frozen in liquid nitrogen and lyophilized, as described previously for other polymeric micelles. See Moretton et al., J. R. Soc. Interface, 9, 487-502 (2012). The lyophilization cake was stored at 4° C. for reconstitution with DD water. To encapsulate doxorubicin (Dox), $Et_3N$-treated Dox (1 mg) was added into 1 mL of graft copolymer solution in NMP and added slowly into DD water as described above. The loading efficiency of Dox under this condition was 10 wt % of the total polymer weight. Higher loading can be obtained by increasing the Dox amount during nanocarrier folding.

To characterize the graft copolymers and the nanocarriers prepared therefrom, gel permeation chromatography (GPC) was performed on a Waters 2695 Alliance® separation model equipped with a RI 2414 (410) detector (Waters Corporation, Milford, Massachusetts, United States of America). The separation of polymer was achieved on a Styrogel® HR4E column (Waters Corporation, Milford, Mass., United States of America, 5 pm, 7.8 mm×300 mm) at 50° C. using dimethyl formamide (DMF) containing 0.1 M LiBr as mobile phase. The molecular weight of the polymer was calibrated against standard PEG ranging from 112 k-0.4 k Dalton. For transmission electron microscope (TEM) characterization, the copper TEM grid (Ted Pella Inc., Redding, Calif., United States of America) was plasma glow-discharged for 20 seconds to create a hydrophilic surface on the carbon surface. Nanocarrier solution (20 μL) was absorbed onto the freshly plasma-discharged carbon membrane for 30 seconds and then blotted with a filter paper to remove excess solution. The grid was examined with a JEOL 2000FX transmission electron microscope (JEOL Ltd., Tokyo, Japan) at 100 kV. The particle size of nanocarrier was measured on the Malvern Zetasizer NanoZS particle sizer (Malvern Instruments Ltd., Malvern, United Kingdom), by dynamic light scattering (DLS).

To monitor the nanocarrier formation, dye merocyanine 540 was added into a serial concentration of micelle solutions (from 0 to 1 mg/mL) to reach a final dye concentration of 40 μM. See Patist et al., J. Surfact Deterg., 3, 53-58 (2000). After equilibrating at room temperature overnight, the absorbance spectra of dye/micelle mixtures were scanned by the microplate reader (Infinite® M200 PRO, Tecan, Mannedorf, Switzerland).

The fluorescence dequenching assay was determined by monitoring the fluorescence spectra of CPT and Dox after disrupting the nanocarrier with surfactant SDS. Briefly, MB-20/Dox nanocarrier was incubated with 1% SDS solution at room temperature. At the indicated time points, the fluorescence spectra of CPT and Dox were scanned, respectively. Dox fluorescence was scanned from the top of well, while CPT signal was detected from the bottom. The spectra were merged by the Graphpad Prism 5 software (Graphpad Software Inc., San Diego, Calif., United States of America).

Discussion: The presently disclosed graft copolymers can be prepared via a facile two-step polymerization, such as illustrated in FIGS. 1A and 2A. Monomers I and II can be polymerized to form a linear alternating multiblock copolymer. For example monomer I can be partially protected tris(2-aminoethyl)amine 2, which can be condensed with monomer II, e.g., bifunctional NHS-PEG$_{5000}$-NHS. Monomer I can also act as a "tee joint" for connection of the linear copolymer with pendant side chains. As shown in FIG. 2A, after removing the Boc protecting group, the third amino group on the "tee joint" monomer I was liberated and then served as an initiation site for side-chain polymerization. The ROP of amino acid N-carboxyanhydrides, facilitated by N-trimethylsilyl (TMS), gradually proceeded on the main chain, leading to the chemically well-defined graft copolymer. CPT was directly polymerized into the side chains through ROP of Glu(CPT)-NCA. Direct polymerization of Glu(CPT)-NCA can provide 100% CPT conjugation to the residues of polyglutamic acid, which maximizes drug loading efficiency and reduces polymer heterogeneity. The more traditional polyglutamic acid CPT conjugation method, can only achieve 20-30% conjugation efficiency (calculated from the loading capacity). See Chen et al., Biomaterials, 33, 1162-1169 (2012); and Singer et al., J. Control Release, 74, 243-247 (2001). Moreover, 100% CPT conjugation in the graft copolymer masks the carboxylic acid residues of polyglutamic acid, making the graft copolymer, as well as the nanocarrier, electrically neutral. The partial conjugation in traditional methods maintains some free carboxylic acid groups and makes the polymer negatively charged, which can adversely affect the cellular uptake and in vivo biodistribution. See He et al., Biomaterials, 31, 3657-3666 (2010); Frolich, Int. J. Nanomedicine, 7, 5577-5591 (2012); and Krasnici et al., Int. J. Cancer, 105, 561-567 (2003).

Figure 3D:
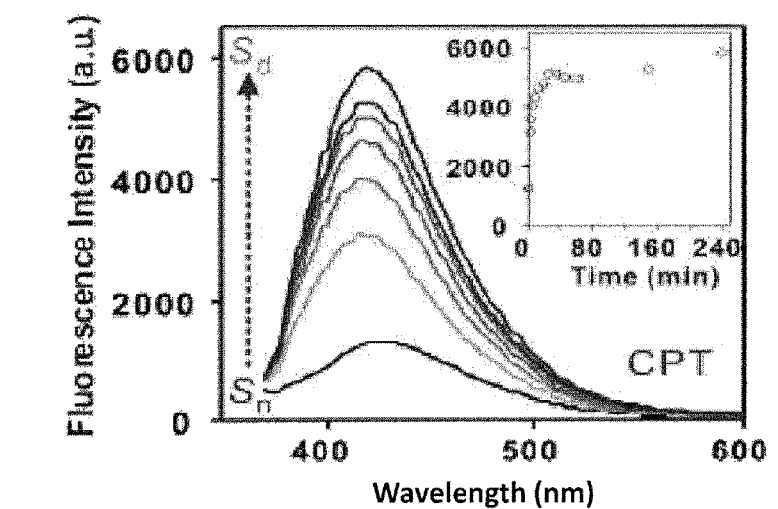
FIG. 3D is a graph showing the fluorescence spectra of camptothecin (CPT) in nanocarriers as described in FIG. 3A wherein the structure of the nanocarriers is disrupted by sodium dodecyl sulfate (SDS). Disruption increases from bottom to top of the group of spectra. The inset shows a plot of the recovery fluorescence intensities over time monitored at excitation/emission wavelengths 370/418 nanometers (nm)
Figure 3E:
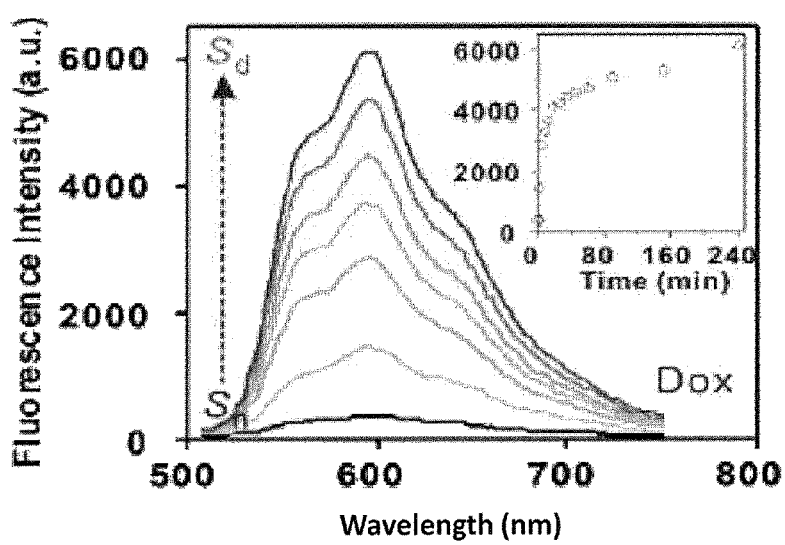
FIG. 3E is a graph showing the fluorescence spectra of doxorubicin (Dox in nanocarriers as described in FIG. 3A wherein the structure of the nanocarriers is disrupted by sodium dodecyl sulfate (SDS). Disruption increases from bottom to top of the group of spectra. The inset shows a plot of the recovery fluorescence intensities over time monitored at excitation/emission wavelengths 480/596 nanometers (nm).
Figure 4:
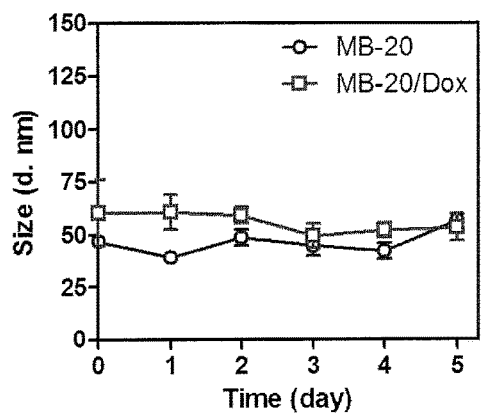
FIG. 4 is a graph showing the hydrodynamic size (diameter, d, in nanometers, nm) of a nanocarrier formed from a graft copolymer of the presently disclosed subject matter prepared using a feed ratio of drug-containing monomer to linear copolymer of 20/1 (i.e., MB-20, circles), or the nanocarrier prepared from the same graft copolymer, only folded in the presence of doxorubicin (MB-20/Dox, squares), over time (0 to 5 days). The hydrodynamic sizes of the nanocarriers were measured by dynamic light scattering (DLS).

The resulting graft copolymer presented a well-controlled structure and relatively narrow distributed molecular weight. See Table 1, below. The content of CPT in the graft copolymer can be readily tuned by the side-chain length, which was controlled by the feed ratios during the second-step polymerization. As shown in Table 1, the graft copolymer MB-10 ("MB" designates multiblock, 10 indicates the second-step polymerization feed ratio of monomer III to linear copolymer is 10/1) showed a CPT loading capacity of 15.2 wt %. By increasing the feed ratio to 20/1 (designated as MB-20), the CPT loading capacity was increased to 23.9 wt %. However, further increasing the feed ratio to 30/1 (designated as MB-30) only slightly enhanced the drug loading capacity (25.1 wt %). Without being bound to any one theory, this could be caused by the declined efficiency of ROP as the side chains elongated. See Deming et al., J. Am. Chem. Soc., 122, 5710-5717 (2000).

into the nanocarriers. The structure of the nanocarriers was characterized by TEM imaging. The nanocarriers folded by MB-20 (Dox: 10 wt %) appeared as monodispersed particles with a diameter of around 50 nm, which was in good agreement with the results determined by the DLS assay. See FIG. 3A. In addition, nanocarriers with either CPT only or with two drugs exhibited good stability at 37° C. up to 5 days. See FIG. 4. The folding process of graft copolymers can be monitored by the dye micellization. See FIG. 3B. Dye merocyanine 540 is known to show a shift of the maximum wavelength ($\lambda_{max}$) during the formation of micelle. See Basu et al., Spectrochim Acta A Mol. Biomol. Spectrosc., 66, 1255-1260 (2007); and Kaschny et al., Eur. J. Biochem., 207, 1085-1091 (1992). As shown in FIG. 3B, the absorbance intensity of the micelled dye peak at 575 nm, associated with a micellar environment, steadily increased as the concentration of the graft copolymer increased, indicating the formation of a micelle-like folded nanostructure. Furthermore, the core-shell corona structure of the nanocarriers was characterized by $^1$H NMR spectra and fluorescence dequenching assay. As shown in FIG. 3C, the proton of CPT, polypeptide and PEG segments were clearly detectable under "$S_d$" in deuterated dimethyl sulfoxide (DMSO-$d_6$). In contrast, only signals associated with PEG were detected under "$S_n$" in deuterated water ($D_2O$), further indicating a core-shell structure of the nanocarrier in water. See Ding et al., ACS Nano, 7, 1918-1928 (2013). The folded structure was also confirmed by fluorescence dequenching measurements, as shown in FIGS. 3D and 3E. When the graft copolymer folded into nanocarriers, the hydrophobic side chains as well as the Dox molecules were expected to stack together to form a hydrophobic core. The drug aggregation in the core caused the "static quenching effect" (see Sung et al., Chem Phys., 179, 23-37 (1994); and Berlier et al., J. Histochem. Cytochem., 51, 1699-1712 (2003)) dramatically decreased the fluorescence intensities of both CPT and Dox, as displayed in FIGS. 3D and 3E. However, when the corona structure was disrupted by adding the surfactant SDS, the fluorescence of CPT and Dox was substantially recovered (from "$S_n$" to "$S_d$").

TABLE 1

Characteristics of polymers and their nanomicelles.

| Sample | $M_w$ (g/mol) | $M_n$ (g/mol) | $M_w/M_n$ | CPT loading (wt %)$^a$ | Size (d · nm) | PDI | CMC$^b$ (mg/mL) |
|---|---|---|---|---|---|---|---|
| Polymer 3 | 30,798 | 21,638 | 1.42 | —/— | —/— | —/— | —/— |
| MB-10 | 34,003 | 23,041 | 1.47 | 15.2 ± 0.4 | 30.3 ± 8.2 | 0.166 | 0.0025 |
| MB-20 | 38,843 | 24,248 | 1.60 | 23.9 ± 0.5 | 62.8 ± 14.4 | 0.158 | 0.0023 |
| MB-30 | 39,899 | 23,301 | 1.71 | 25.1 ± 0.4 | 65.1 ± 15.5 | 0.137 | 0.0023 |

$^a$wt % is expressed as weight percentage of CPT in polymer
$^b$The cmc was determined by eosin Y mediated dye micellization method described in Binaschi et al., Stem Cells, 13, 369-379 (1995)

To fold the graft copolymer and encapsulate Dox, graft copolymer and Dox were dissolved into organic solvent NMP and then simply mixed with large quantities of water. Together with Dox encapsulation, the folding proceeded instantly and efficiently. All the three graft copolymers showed strong encapsulation capability toward Dox. Within MB-20's folding, as much as 30.0 wt % of Dox (percentage of Dox weight compared to polymer) can be encapsulated Example 5

In Vitro Drug Release and Cytotoxicity

The release of CPT from nanocarrier was monitored in 100% mouse serum by HPLC. Briefly, MB-20 solution (or Glu(CPT)-OH solution) was mixed with 200% mouse serum to achieve a final concentration of 40 µM (CPT equivalent).

The mixtures were incubated at 37° C. At various time points, 20 µL of aliquots were sampled and precipitated with 80 µL of acetonitrile containing 0.5% TFA. After 10 min of incubation, the precipitate was spun down at 20,000 g for 10 min and the supernatant was analyzed by HPLC for quantification of the released CPT. The HPLC system was equipped with Agilent pump (Agilent Technologies, Santa Clara, Calif., United States of America), controller, autosampler and detector. The sample was analyzed on Waters C-18 reverse phase column (Waters Corporation, Milford, Mass., United States of America) 4.6×250 mm, 5 µm) with a mobile phase of acetonitrile/water (v/v, 35/65) plus 0.1% formic acid. The flow rate was set at 1 mL/min and absorbance of CPT was monitored at 370 nm.

The release of Dox was conducted using a dialysis method in phosphate buffer (50 mM, pH 5.0 and 7.4) previously reported. See Ding et al., ACS Nano, 7, 1918-1928 (2013). MB-20/Dox in different pH phosphate buffers (400 µL, final concentration: 5 µM) was sealed in the dialysis tubing with MWCO 14 kDa and was dialyzed against 25 mL of the corresponding pH phosphate buffer with stirring at 37° C. At various time points, 100 µL of release media was sampled for fluorescence quantification of Dox (Ex/Em=480/596 nm), and then returned to the release media to maintain a constant volume. The release experiments were conducted in triplicate.

In vitro cytotoxicity of CPT, Dox, MB-20 and MB-20/Dox was measured using the 3-(4,5-dimethylthiazol-2-yl)-2,5-diphenyltetrazolium bromide (MTT) assay. Briefly, cancer cells were seeded in a 96-well plate at a density of 5,000 cells per well. After 12 h incubation, a series of drug dilution (1 nM to 300 µM) were added into wells. After 48 h of drug treatment, the cytotoxicity was measured using the MTT assay. To enhance the assay sensitivity, Sorensen's glycine buffer (0.1 M glycine, 0.1 M NaCl adjust pH to 10.5 with 0.1 N NaOH) was added into wells before absorbance assay. See Plumb et al., Cancer Res., 49, 4435-4440 (1989); Tai et al., Mol. Pharm., 8, 901-912 (2011); and Tai et al., Mol. Pharm., 10, 477-487 (2013). The absorbance at wavelength of 570 nm was measured using a microplate reader (Infinite® M200 PRO, Tecan, Mannedorf, Switzerland). The half-maximal inhibitory concentration ($IC_{50}$) was calculated by fitting a concentration—absorbance curve using the Graphpad Prism 5 software (Graphpad Software Inc., San Diego, Calif., United States of America).

For in vitro cellular uptake study, A549 cells were seeded into 6-well plate one day before uptake study. When it was confluent, the monolayer was washed twice with FBS-free DMEM media and subsequently incubated with MB-20/Dox solution in DMEM (100 µM, CPT equivalent) at 37° C. At the indicated time points, the drug was removed and the monolayer was washed four times with DPBS. The cells were lysed with 0.5 mL of 1% SDS solution for 10 min at room temperature. The viscous solution was transferred into a 1.5 mL centrifuge tube and sonicated for 2 cycles (1 s each with a duty cycle of 20%). The drug concentration in the cell lysate was quantified by fluorescence plate reader (CPT: Ex/Em=370/450 nm; Dox: Ex/Em=480/596 nm). The total protein concentration of cell lysate was measured by the BCA protein assay kit (Sigma, St. Louis, Mo., United States of America), and the cellular uptake was normalized to the total amount of cell protein for each sample.

To study the endocytotic pathway, the cells were pretreated with sucrose (450 mM), chlorpromazine (30 µM), nystatin (25 µg/mL), methyl-β-cyclodextrin (3 mM), sodium azide/2-deoxyglucose (0.1%/50 mM) and wortmannin (0.8 mM) in serum-free DMEM media for 1 h at 37° C., respectively. See Xiao et al., Biomaterials, 32, 5148-5157 (2011). Nanocarriers were then added into each well at CPT equivalent concentration of 6 µM and incubated with cells for another 2 h in the presence of inhibitors. The cell monolayer was then washed and lysed. The drug concentrations in the lysate were quantified as described above.

To track the intracellular location of nanocarrier, the fluorescence of CPT and Dox in cancer cells was monitored by confocal laser scanning microscope (CLSM). Briefly, A549 cells (40,000 cells) were seeded in a confocal microscope dish (MatTek Corporation, Ashland, Mass., United States of America) one day before experiments. Cell monolayer was then washed with serum-free DMEM and incubated with MB-20/Dox in DMEM (4 µM CPT equivalent) at 37° C. At the various time points, drugs were removed and the late endosomes and lysosomes were stained with LysoTracker® Green DND-26 (50 nM) for 30 min (Life Tech, Grand Island, N.Y., United States of America). The intracellular distribution of nanocarrier was observed by CLSM (LSM 710, Zeiss, Jena, Germany).

Figure 5A:
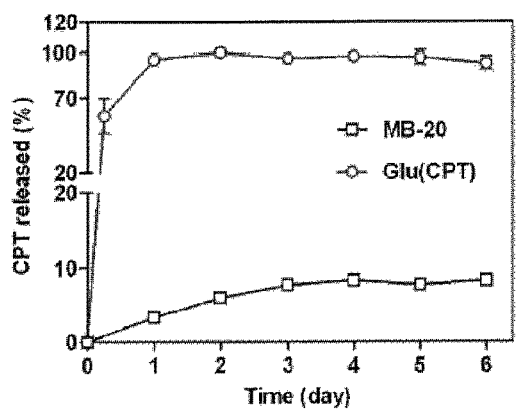
FIG. 5A is a graph of camptothecin (CPT) release from glutamic acid-CPT conjugate (circles) or a nanocarrier formed from a graft copolymer of the presently disclosed subject matter prepared using a feed ratio of CPT-containing monomer to linear copolymer of 20/1 (i.e., MB-20, squares) in 100% mouse serum at 37° C. The nanocarrier has the same ester drug linkage as the glutamic acid-CPT conjugate. However, the ester linkage in the nanocarrier is protected by polyethylene glycol (PEG) in the nanocarrier shell, preventing esterase attack and resulting in improved stability in the serum.
Figure 5B:
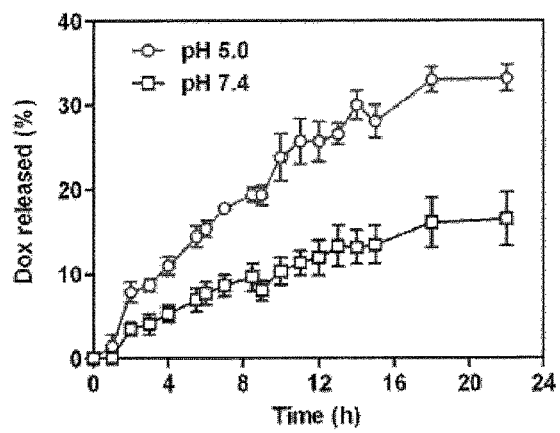
FIG. 5B is a graph showing the release of doxorubicin (Dox) from a DOX-containing nanocarrier of the presently disclosed subject matter over time (0 to 24 hours) at different pHs (i.e., pH 5.0, circles; or pH 7.4, squares) at 37° C.

Discussion: The in vitro CPT release kinetics of MB-20 were quantified by HPLC. The data in FIG. 5A indicates that less than 10% of CPT was released from nanocarriers in the presence of the mouse serum within 6 days, indicating its high stability in the serum. In sharp contrast, Glu(CPT)-OH, the monomer III derivative, showed a burst release profile of CPT, although they had the same drug-ester linker, which provided evidence that the presence of PEG shell of MB-20 was able to effectively shield off esterase attack and prevent from premature drug release. In addition, the encapsulated Dox displayed a preferential release under a weak-acid condition, as depicted in FIG. 5B. This accelerated release under an acidic condition was attributed to the re-protonation of the amino group of Dox and its subsequently higher aqueous solubility at a lower pH value. See Shuai et al., J. Control Release, 98, 415-426 (2004); and Kataoka et al., J. Control Release, 64, 143-153 (2000). [59-60]. Provided that the nanocarriers were trapped in endosomes (pH 5-6) and lysosomes (pH 4-5) after cellular uptake, the acid-facilitated release can be a benefit to the enhanced cytotoxicity.

As shown in Table 2, below, MB-20 and MB-20/Dox exhibited potent in vitro cytotoxicity against a panel of 9 cancer cell lines. CPT showed potent cytotoxicity in most of the cancer cell lines, with $IC_{50}$s ranging from 0.02 to 3.30 µM. Interestingly, MB-20 exhibited comparable or only slightly weaker potency than CPT, except in cell line MDA-MB-231. Since the ester linker cleavage is the prerequisite for MB-20 to elicit its activity, the results demonstrate that the CPT of the nanocarriers is releasable in cancer cells. After co-delivery with Dox, nanocarrier MB-20/Dox presented as 1.5- to 60-fold more potent than MB-20, confirming the enhanced anticancer efficacy of the co-delivery system.

TABLE 2

In vitro cytotoxicity ($IC_{50}$, µM). The cancer cells were treated with the agents for 48 hours before MTT assay. Values shown are mean ± SD.

| Cancer Type | Cell Line | CPT | Dox | MB-20[a] | MB-20/Dox[a] |
|---|---|---|---|---|---|
| Breast | MCF-7 | 1.2 ± 1.0 | 0.3 ± 1.0 | 6.7 ± 1.2 | 2.1 ± 1.3 |
|  | MDA-MB-231 | 0.6 ± 0.5 | 0.1 ± 0.6 | 17.5 ± 0.7 | 0.3 ± 0.6 |
|  | MDA-MB-468 | 0.09 ± 0.09 | 0.1 ± 1.1 | 0.3 ± 1.5 | 0.2 ± 1.6 |

TABLE 2-continued

In vitro cytotoxicity ($IC_{50}$, µM). The cancer cells were treated with the agents for 48 hours before MTT assay. Values shown are mean ± SD.

| Cancer Type | Cell Line | CPT | Dox | MB-20[a] | MB-20/Dox[a] |
|---|---|---|---|---|---|
| Lung | A549 | 0.3 ± 1.0 | 0.5 ± 0.8 | 1.2 ± 1.0 | 0.8 ± 1.1 |
|  | NCI-H441 | 0.1 ± 0.2 | 0.2 ± 0.4 | 0.3 ± 0.4 | 0.2 ± 0.4 |
| Liver | Hep G2 | 0.6 ± 1.4 | 0.5 ± 1.4 | 2.0 ± 1.5 | 1.0 ± 1.1 |
| Prostate | PC-3 | 0.02 ± 0.3 | 0.2 ± 0.4 | 0.3 ± 0.5 | 0.1 ± 0.3 |
| Cervix | HeLa | 3.3 ± 1.5 | 1.0 ± 1.7 | 6.2 ± 1.7 | 2.3 ± 1.8 |
| Leukemia | HL-60[b] | 0.4 ± 1.0 | 0.3 ± 1.0 | 1.0 ± 0.2 | 0.3 ± 0.2 |

[a]The $IC_{50}$ values are expressed in term of CPT equivalent
[b]The $IC_{50}$ values of this suspension cell line were determined by CellTiter-Glo ® Luminescent Cell Viability Assay (Promega, Madison, Wisconsin, United States of America)

The drug accumulation and subcellular localization of nanocarriers were determined by the in vitro uptake study and CLSM observation. As shown in FIG. 6A, the accumulated uptake of CPT and Dox in A549 cells was gradually increased over the uptake time. Moreover, the molar ratio of the cellular accumulated CPT and Dox at most time points in FIG. 6A was around 2.1/1, which well agreed with the drugs' molar ratios in the nanocarriers, indicating that the nanocarrier was internalized by the cancer cells without significant premature leakage of Dox.

To elucidate the uptake pathway of the nanocarrier, several specific endocytic inhibitors were used. As shown in FIG. 6B, sucrose and chlorpromazine (clathrin-mediated endocytosis inhibitors; see Heuser et al., J. Cell Biol. 108, 389-400 (1989); and Wanq et al., J. Cell Biol., 123, 1107-1117 (1993)) reduced the uptake of nanocarrier by about 70% and 50%, respectively. In contrast, insignificant inhibition on the cellular uptake of nanocarrier was found in the cells pretreated with nystatin (an inhibitor of caveolin-mediated endocytosis; see Singh et al., Mol. Biol. Cell., 14, 3254-3265 (2003)) or sodium azide/2-deoxyglucose and wortmannin (inhibitors of micropinocytosis; see Nishimura et al., J. Biol. Chem., 283, 11752-11762 (2008); and Araki et al., J. Cell Biol., 135, 1249-1260 (1996)). Additionally, the uptake of nanocarrier was strongly inhibited by the lipid raft inhibitor, methyl-β-cyclodextrin. See Kabouridis et al., Eur. J. Immunol., 30, 954-963 (2000). Similar phenomenon have been observed in the cellular uptake of other polymeric micelles. See Xiao et al., Biomaterials, 32, 5148-5157 (2011). Without being bound to any one theory, these results indicate that lipid raft and clathrin-mediated endocytosis play a role in the internalization of the nanocarrier. Similar to the observation of in vitro uptake study in FIG. 6A, the fluorescence of CPT and Dox in cells gradually increased until reaching a plateau at 4 h. The CLSM images at 1 h pointed out that the fluorescence of CPT and Dox was well merged with that of LysoTracker, revealing that nanocarriers were mainly localized in the acidic organelles (endosomes and lysosomes) at the first 2 h of incubation. After 4 h of incubation, parts of drugs migrated outside from endosomes/lysosomes as evidenced by the presence of CPT and Dox fluorescence beyond acidic organelles. Further incubation lead to more escape of drugs from lysosomes at 8 h. A considerable amount of nanocarriers/drugs were still trapped in the acidic organelles, which, without being held to any one theory, could be attributed to the lack of endosome/lysosome disrupting feature in the nanocarrier. However, the lysosome can play a role in the drug release. The free drugs can be released through degradation of polymers by lysosomal enzymes, followed by diffusion of the active agents into the cytoplasm.

Example 6

In Vivo Targeting and Activity

For near-infrared optical imaging of micelles in tumor-bearing mice, the graft copolymer was labeled with Cy5.5-NHS ester via methods analogous to those previously reported. See Tsai et al., Biomaterials, 31, 2293-2301 (2010); and Chen et al., Biomaterials, 33, 4576-4588 (2012). Briefly, 20 µL of Cy5.5-NHS solution in chloroform (2.5 mg/mL) was added into 1 mL of graft copolymer solution in NMP (10 mg/mL). The reaction was stirred in the dark at room temperature overnight, and then 500 µL of phosphate buffered saline (PBS) was added. The reaction was stirred for another 5 h and then the Cy5.5 labeled graft copolymer was folded into a nanocarrier as described above. The nanocarrier solution was dialyzed against DD water for 48 h to remove the organic solvent and free Cy5.5. After passage through a 0.45 µm syringe filter, the micelle solution was lyophilized with cryoprotectant HPβCD (1%).

Female naive athymic nude mouse (Strain name, J:NU) was purchased from Jackson Laboratory (Bar Harbor, Me., United States of America). A tumor xenograft was established in the right dorsum of the nude mice by injecting 200 µL of A549 cells/Matrigel mixture ($5 \times 10^6$ cells per mouse; v/v=1/1) (BD Biosciences, San Jose, California, United States of America). When tumors reached 300-400 mm$^3$, mice were intravenously injected with MB-20/Cy5.5 nanocarrier at the Cy5.5 dose of 26 nmol/kg. Near-infrared (near-IR) optical images were taken on an IVIS® Lumina imaging system (Caliper Life Sciences, Hopkinton, Mass., United States of America) at 4, 24, 48 hand 72 h post injection. At 72 h post injection, the mice were euthanized, and tumors as well as other tissues were harvested for ex vivo imaging. Region-of-interest (ROI) was circled around the organs, and the fluorescence intensities were analyzed by Living Image Software.

A tumor xenograft was established in the right dorsum of the nude mice as described above. Seventeen days after implantation when tumors reached an average volume of 80-100 mm$^3$, treatment was initiated by giving multiple doses (once every four days for a total of six injections) of PBS, free CPT (5 mg/kg), free Dox (5 mg/kg), MB-20 (10 mg/kg, CPT equivalent) and MB-20/Dox (10 mg/kg, CPT equivalent). All the groups were intravenously injected via the tail vein with the exception of CPT (intraperitoneal injection) due to its low solubility. The tumor sizes and body weights were closely monitored every other day from the ninth day after implantation. The tumor volume for each time point was calculated using the following formulation: length×width$^2$/2.

Figure 7A:
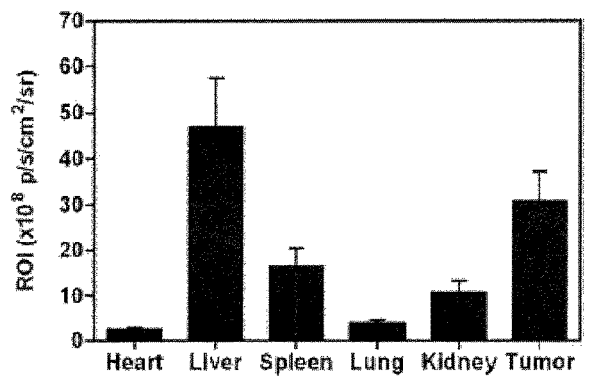
FIG. 7A is a bar graph of the quantitative analysis of fluorescence signals from tumors and other tissues in A549 tumor-bearing nude mice 72 hours after intravenous injection of a fluorescence labeled nanocarrier of the presently disclosed subject matter, formed from a graft copolymer prepared using a feed ratio of camptothecin (CPT)-containing monomer to linear copolymer of 20/1 (MB-20). Values are means ±standard deviation (SD) for three mice. *P<0.05 with respect to heart, spleen, and kidney groups.

Discussion: The in vivo accumulation of nanocarrier in tumor was evaluated by near-IR optical imaging. The N-terminals of the side chains in the graft copolymer MB-20 were labeled with Cy5.5, and the resulting graft copolymer was folded into nanocarriers, which were then intravenously administered into mice bearing the A549 tumor model. The mice receiving MB-20/Cy5.5 nanocarriers displayed strong fluorescence at the tumor sites after 4 h. To assess biodistribution, tumors and other tissues were harvested for ex vivo imaging at 72 h post injection. The quantitative analysis in FIG. 7A showed that the tumor exhibited significantly higher accumulation of nanocarrier than heart, spleen and kidney.

Figure 7B:
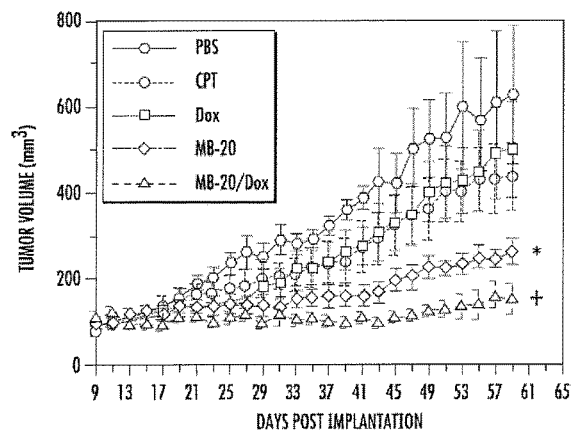
FIG. 7B is a graph of A549 tumor growth curves after treating A549 tumor-bearing nude mice with either phosphate buffered saline (PBS, hexagons), camptothecin (CPT, circles), doxorubicin (Dox, squares), a nanocarrier of the presently disclosed subject matter formed from a graft copolymer prepared using a feed ration of CPT-containing monomer to linear copolymer of 20/1 (MB-20, diamonds), or the MB-20 nanocarrier encapsulating doxorubicin (MB-20/Dox, triangles). Tumor volume (cubic millimeters, $mm^3$) values are means±standard error of the mean (SEM) from five mice. *P<0.05 compared to PBS, CPT, and Dox groups; +P,0.05 compared to MB-20.
Figure 7C:
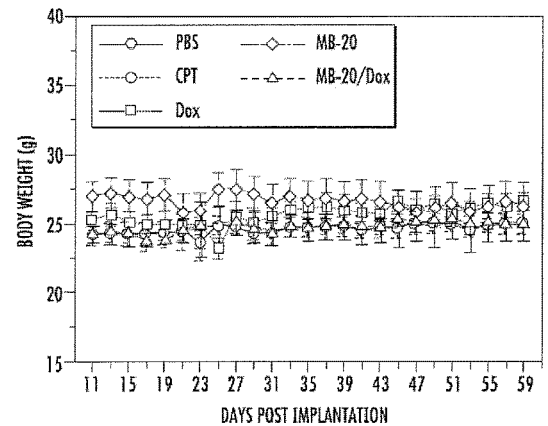
FIG. 7C is a graph of body weight (grams, g) variation of A549 tumor-bearing nude mice treated with either phosphate buffered saline (PBS, hexagons), camptothecin (CPT, circles), doxorubicin (Dox, squares), a nanocarrier of the presently disclosed subject matter formed from a graft copolymer prepared using a feed ration of CPT-containing monomer to linear copolymer of 20/1 (MB-20, diamonds), or the MB-20 nanocarrier encapsulating doxorubicin (MB-20/Dox, triangles).

Further, the anticancer efficacy of nanocarriers was assessed toward A549 tumor-bearing nude mice via tail vain injection of different formulations. Compared with the groups treated with PBS, CPT and Dox, the single-drug nanocarrier MB-20 and dual-drug nanocarrier MB-20/Dox possessed significantly higher anti-tumor activities (see FIG. 7B), regardless of their comparable $IC_{50}$ values on cancer cells in vitro. See Table 2. Noticeably, the dual-drug nanocarrier exhibited a significantly higher tumor inhibition than single-drug loaded MB-20. Moreover, the current delivery platform can increase the administration dose of CPT to more than 10 mg/kg, which is usually intolerable by mice if injected as a free drug. See Schluep et al., Clin. Cancer Res., 12, 1606-1614 (2006). These results revealed that graft copolymer folded nanocarrier produced measurable inhibitory effect on tumor growth, and, without being bound to any one theory, therapeutic efficacy could be attributed to superior accumulation at tumor sites and insignificant toxicity in vivo. See FIG. 7C.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A graft copolymer drug conjugate, wherein the graft copolymer drug conjugate has the formula:

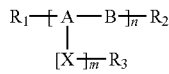

wherein:
A is a trivalent moiety;
B comprises a hydrophilic polymeric moiety;
X is a divalent moiety comprising a covalently attached first therapeutic agent, wherein X is derived from a monomer that comprises a moiety that can undergo ring opening polymerization and wherein said monomer comprises the covalently attached first therapeutic agent;
n is an integer between 4 and 25;
m is an integer between 5 and 30; and
each of $R_1$, $R_2$, and $R_3$ is a monovalent moiety.

2. The graft copolymer drug conjugate of claim 1, wherein the first therapeutic agent is covalently attached via a linkage that can be enzymatically cleaved and/or that can be cleaved under physiological conditions at a desired location in vivo.

3. The graft copolymer drug conjugate of claim 1, wherein the first therapeutic agent is covalently attached via a linkage that can be cleaved via an intracellular esterase.

4. The graft copolymer drug conjugate of claim 1, wherein the first therapeutic agent is selected from the group consisting of a chemotherapeutic agent, an anti-viral agent, an anti-inflammatory agent, an analgesic agent, an anesthetic, an antifungal agent, an antibiotic, an antihypertensive, an antimicrobial, an antipyretic, a cardioactive agent, a vasoconstrictor, a vasodilator, a nutritional supplement, an antiarthritic, a diuretic, a hormone, a radiation sensitizer, a sedative and a therapeutic biological agent.

5. The graft copolymer drug conjugate of claim 1, wherein A is derived from a trifunctional monomer comprising three chemically reactive functional groups wherein each of the three functional groups is independently selected from the group consisting of hydroxyl, amino, thiol, alkyl or aryl disulfide, isothiocyanate, thiocarbonylimidazole, thiocarbonylchloride, aldehyde, ketone, carboxylic acid, carboxylic acid ester, sulfonic acid, sulfonic acid ester, sulfonyl chloride, phosphoric acid, alkyl or aryl succinimidyl carbonate, alkyl or aryl chlorocarbonate, alkyl or aryl succinimidylthiocarbonate, alkyl or aryl chlorothiocarbonate, halide, and thioester.

6. The graft copolymer drug conjugate of claim 1, wherein A is derived from a natural or non-natural amino acid or from a tris(aminoalkyl)amine.

7. The graft copolymer drug conjugate of claim 1, wherein the hydrophilic polymeric moiety is selected from the group consisting of poly(alkylene glycol), poly(vinyl alcohol), poly(2-hydroxyethyl methacrylate), poly[N-(2-hydroxypropyl)methacrylamide] (PHPMA), poly(acrylic acid), poly(methacrylic acid), poly(maleic acid), polylysine, dextran, chitosan, alginate, hyaluronic acid, and combinations thereof.

8. The graft copolymer drug conjugate of claim 1, wherein B comprises a poly(ethylene glycol) (PEG).

9. The graft copolymer drug conjugate of claim 1, wherein X is derived from a monomer comprising the N-carboxyanhydride derived from an amino acid-first therapeutic agent conjugate, wherein said amino acid-first therapeutic agent conjugate comprises an amino acid covalently attached to the first therapeutic agent via a functional group on the amino acid side chain, optionally wherein the amino acid is glutamic acid and the amino acid-first therapeutic agent conjugate is glutamic acid covalently attached to the first therapeutic agent via the carboxylic acid side chain.

10. The graft copolymer drug conjugate of claim 1, wherein said graft copolymer drug conjugate has the formula:

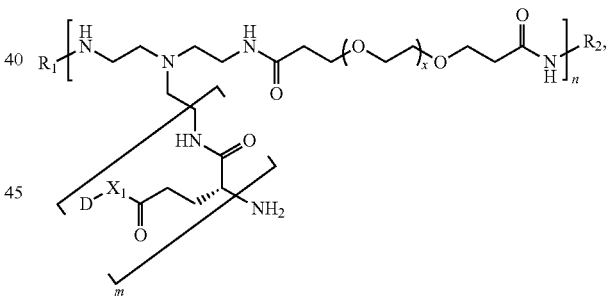

wherein:
n is an integer between 4 and 25;
m is an integer between 5 and 30;
x is an integer between 10 and 200, optionally wherein x is 112;
$X_1$ is O, S, or NH;
D is a monovalent moiety derived from the first therapeutic agent; and
$R_1$ and $R_2$ are each monovalent moieties.

11. The graft copolymer drug conjugate of claim 1, wherein the graft copolymer drug conjugate comprises between about 10 and about 30 weight percentage (%) of the first therapeutic agent.

12. The graft copolymer drug conjugate of claim 1, wherein the graft copolymer drug conjugate has a mass average molecular mass (Mw) between about 30,000 g/mol and about 40,000 g/mol.

13. The graft copolymer drug conjugate of claim 1, wherein the graft copolymer drug conjugate has a critical micelle concentration (CMC) of between about 0.002 mg/mL and about 0.003 mg/mL.

14. A polymeric micelle comprising a graft copolymer drug conjugate of claim 1.

15. The polymeric micelle of claim 14, wherein the polymeric micelle has a particle size polydispersity index (PDI) of between about 0.1 and about 0.2, optionally between about 0.13 and about 0.17.

16. The polymeric micelle of claim 14, further comprising at least a second therapeutic agent encapsulated non-covalently within the micelle.

17. The polymeric micelle of claim 16, wherein the first and second therapeutic agents are both chemotherapeutic agents.

18. The polymeric micelle of claim 17, wherein the first and second therapeutic agents are both topoisomerase (Top) inhibitors, optionally wherein the first therapeutic agent is a Top I inhibitor and the second therapeutic agent is a Top II inhibitor.

19. The polymeric micelle of claim 18, wherein the first therapeutic agent is camptothecin and the second therapeutic agent is doxorubicin.

20. The polymeric micelle of claim 16, comprising up to about 30 weight percentage (%) of the second therapeutic agent (compared to the weight of graft copolymer drug conjugate).

21. The polymeric micelle of claim 14, wherein the micelle has an average diameter of between about 10 nm and about 100 nm.

22. A pharmaceutical composition comprising a graft copolymer drug conjugate of claim 1, and further comprising a pharmaceutically acceptable carrier.

23. The pharmaceutical composition of claim 22, wherein the composition comprises a polymeric micelle comprising covalently attached first therapeutic agent and an encapsulated second therapeutic agent, and wherein the first and second therapeutic agents have different release profiles.

24. A method of treating a disease in a subject in need thereof, the method comprising administering to the subject a pharmaceutical composition of claim 22.

25. The method of claim 24, wherein the disease is cancer.

26. A method of treating cancer in a subject in need thereof, the method comprising administering to the subject a pharmaceutical composition of claim 23.

27. The method of claim 26, wherein the first and second therapeutic agents have synergistic effects and/or wherein the micelle preferentially accumulates in cancer cells when administered to the subject as compared to non-cancerous heart, spleen and/or kidney cells.

* * * * *